United States Patent
Sun et al.

(10) Patent No.: US 12,077,566 B2
(45) Date of Patent: Sep. 3, 2024

(54) **MUTANTS OF RECOMBINANT IMMUNOREGULATORY PROTEIN OF *GANODERMA LUCIDUM* AND APPLICATIONS THEREOF**

(71) Applicants: Xitian Zhang, Jilin (CN); Fei Sun, Jilin (CN); Xin Zhang, Jilin (CN)

(72) Inventors: Fei Sun, Jilin (CN); Chongyang Liang, Jilin (CN)

(73) Assignees: Xitian Zhang, Jilin (CN); Fei Sun, Jilin (CN); Zin Zhang, Jilin (CN)

( * ) Notice: Subject to any disclaimer, the term of this patent is extended or adjusted under 35 U.S.C. 154(b) by 281 days.

(21) Appl. No.: 16/462,941

(22) PCT Filed: Mar. 14, 2018

(86) PCT No.: PCT/CN2018/078934
§ 371 (c)(1),
(2) Date: May 22, 2019

(87) PCT Pub. No.: WO2018/184448
PCT Pub. Date: Oct. 11, 2018

(65) Prior Publication Data
US 2019/0352345 A1   Nov. 21, 2019

(30) Foreign Application Priority Data
Apr. 8, 2017 (CN) .......................... 201710226093.3

(51) Int. Cl.
*C07K 14/375* (2006.01)
*A61K 38/00* (2006.01)
(Continued)

(52) U.S. Cl.
CPC ............ *C07K 14/375* (2013.01); *A61P 35/00* (2018.01); *A61P 35/04* (2018.01); *A61K 38/00* (2013.01); *A61K 38/1754* (2013.01)

(58) Field of Classification Search
CPC .. C07K 14/375; A61K 38/00; A61K 38/1754; A61K 35/00; A61K 35/04; A61P 35/00; A61P 35/04
See application file for complete search history.

(56) References Cited

U.S. PATENT DOCUMENTS

2006/0275312 A1 * 12/2006 Chua ........................ A61P 37/04
536/23.7
2011/0318429 A1   12/2011 Ko
(Continued)

FOREIGN PATENT DOCUMENTS

| CN | 104817634 A | 8/2015 |
| CN | 104817637 A | 8/2015 |

(Continued)

OTHER PUBLICATIONS

Lieuwe G. Van Der Hem et al., Ling ZHI-8: Studies of a New Immunomodulating Agent, Transplantation, 1995, pp. 438-443, vol. 60, No. 5—Made of record in IDS filed May 22, 2019 (Year: 1995).*

(Continued)

*Primary Examiner* — Gary B Nickol
*Assistant Examiner* — Amelia Nicole Dickens
(74) *Attorney, Agent, or Firm* — Merchant & Gould P.C.

(57) ABSTRACT

Mutants of recombinant immunoregulatory protein of *Ganoderma lucidum* (rLZ-8) and applications thereof are provided. It is found by the present invention that: an anti-EGFR (epidermal growth factor receptor) domain exists in a structure of the rLZ-8; particularly, the domain through positive potential characteristics thereof induces a killing effect to an abnormal EGFR-expressed tumor. Based on the above scientific discovery, with utilizing computational
(Continued)

simulation technology, the mutants of the rLZ-8, having better antitumor effects, are obtained.

9 Claims, 10 Drawing Sheets

Specification includes a Sequence Listing.

(51) Int. Cl.
*A61K 38/17* (2006.01)
*A61P 35/00* (2006.01)
*A61P 35/04* (2006.01)

(56) References Cited

U.S. PATENT DOCUMENTS

| | | | |
|---|---|---|---|
| 2012/0003259 A1 | 1/2012 | Chua et al. | |
| 2016/0289280 A1 | 10/2016 | Zhang et al. | |
| 2017/0080048 A1* | 3/2017 | Hsu | A61K 38/16 |
| 2017/0173110 A1* | 6/2017 | Ko | A61P 35/00 |
| 2017/0368119 A1 | 12/2017 | Wu et al. | |

FOREIGN PATENT DOCUMENTS

| | | | |
|---|---|---|---|
| CN | 104892735 A | 9/2015 | |
| CN | 106188255 A | 12/2016 | |
| CN | 106432442 A | 2/2017 | |
| EP | 3 034 515 A1 | 6/2016 | |
| JP | 5-68561 A | 3/1993 | |
| JP | 05068561 A * | 3/1993 | |
| WO | WO 2004/092210 A2 | 10/2004 | |
| WO | WO 2015/058536 A1 | 4/2015 | |
| WO | WO-2015055026 A1 * | 4/2015 | A61K 36/074 |
| WO | WO 2015/135483 A1 | 9/2015 | |
| WO | WO-2015192663 A1 * | 12/2015 | A61K 38/16 |
| WO | WO 2016/034081 A1 | 3/2016 | |

OTHER PUBLICATIONS

Gordan et al. "And What Other Medications Are You Taking?", Apr. 10, 2011, Journal of Clinical Oncology, vol. 29 No. 11, p. e288-e291. (Year: 2011).*
"Effective dose (pharmacology)", archived by The Wayback Machine Nov. 13, 2016, Wikipedia, p. 1-2. (Year: 2016).*
Lin et al. "Dimerization of the N-terminal Amphipathic a-Helix Domain of the Fungal Immunomodulatory Protein from Ganoderma tsugae (Fip-gts) Defined by a Yeast Two-hybrid System and Site-directed Mutagenesis", Aug. 8, 1997, Journal of Biological Chemistry, vol. 272 No. 32, p. 20044-20048. (Year: 1997).*
Gunner et al. "Backbone Dipoles Generate Positive Potentials in all Proteins: Origins and Implications of the Effect", Mar. 2000, Biophysical Journal, 78: p. 1126-144. (Year: 2000).*
Bao et al. "Computational Insights into the Molecular Mechanism of the High Immunomodulatory Activity of LZ-8 Protein Isolated from the Lingzhi or Reishi Medicinal Mushroom Ganoderma lucidum (Agaricomycetes)", Jan. 1, 2018, International Journal of Medicinal Mushrooms, 20(6): p. 537-548. (Year: 2018).*
Huang et al. "Crystal structure of LZ-8 from the medicinal fungus Ganoderma lucidium", Dec. 11, 2008, Proteins, vol. 75 No. 2, p. 524-527. (Year: 2008).*
Lieuwe G. Van Der Hem et al., Ling ZHI-8: Studies of a New Immunomodulating Agent, Transplantation, 1995, pp. 438-443, vol. 60, No. 5.
Chien-Ting Wu et al., Ling Zhi-8 mediates p53-dependent growth arrest of lung cancer cells proliferation via the ribosomal protein S7-MDM2-p35 pathway, Carcinogenesis, 2011, pp. 1890-1896, vol. 32, No. 12.
Tung-Yi Lin et al., Induction of Cbl-dependent epidermal growth factor receptor degradation in Ling Zhi-8 suppressed lung cancer, International Journal of Cancer, 2017, pp. 2596-2607, vol. 140.
Chongyang Liang et al., Recombinant Lz-8 from Ganoderma lucidum induces endoplasmic reticulum stress-mediated autophagic cell death in SGC-7901 human gastric cancer cells, Oncology Reports 27, 2012, pp. 1079-1089.
Extended European Search Report issued Jan. 19, 2022 in European Patent Application No. 18780732.6, 11 pages.

* cited by examiner

1 Detector A Channel 1/280nm

MUTANTS OF RECOMBINANT IMMUNOREGULATORY PROTEIN OF *GANODERMA LUCIDUM* AND APPLICATIONS THEREOF

CROSS REFERENCE OF RELATED APPLICATION

This is a U.S. National Stage under 35 U.S.C 371 of the International Application PCT/CN2018/078934, filed Mar. 14, 2018, which claims priority under 35 U.S.C. 119(a-d) to CN 201710226093.3, filed Apr. 8, 2017.

BACKGROUND OF THE PRESENT INVENTION

Field of Invention

The present invention relates to optimization and modification for protein mutation made by computational simulation technology.

Description of Related Arts

The human epidermal growth factor receptor (EGFR) is the transmembrane receptor having a molecular weight of 170 kDa, which is encoded by the proto-oncogenes and shows the inherent tyrosine kinase activity. The epidermal growth receptor (EGF), transforming growth factor alpha (TGF-α), amphiregulin, heparin-binding EGF and β-tunicin are all ligands binding with the EGFR. After being activated by the ligands, the EGFR regulates many cellular processes through the signal transduction pathway mediated by the tyrosine kinase. The cellular processes include but are not limited to processes of activating and controlling cell proliferation, cell differentiation, cell survival and programmed cell death.

A large number of studies have shown that: although the EGFR can express in the cells of normal tissues, the expression quantity is low; however, the EGFR has the abnormal overexpression at the surface of many cancer cells, such as the lung cancer, breast cancer and colorectal cancer. For the phenomenon characteristics that the EGFR activates the proliferation and differentiation of the cancer cells through the ligands after the overexpression of the EGFR, the small molecule drugs and antibodies which have been available on the market target the EGF binding sites of the extracellular part or the tyrosine kinase active sites of the intracellular part of the targeting EGFR. The small-molecule tyrosine kinase inhibitors such as gefitinib and Erlotinib can block the autophosphorylation of the EGFR and inhibit the transduction of the downstream signal. On the other hand, the monoclonal antibody targeting the extracellular part of the targeting EGFR can block the binding of the ligands and inhibit the activation of the downstream pathway such as the cell proliferation. The internalization of the EGFR caused by the antibody has been gradually paid attention by the researchers in the field. The research on the EGFR internalization provides the development strategy for the biological medicines with the EGFR as the target.

Since the last century, the internalization behavior of the EGFR has been widely researched. The endocytosis of the EGFR mainly has two ways, wherein the first way is the endocytosis relying on the clathrin and the second way is the endocytosis without relying on the clathrin. When the EGF having the low concentration simulates, the endocytosis of the EGFR is medicated by the clathrin. When the EGF having the high concentration simulates, the endocytosis of the EGFR is mainly through the clathrin-independent way, comprising the caveolae endocytosis and the macropinocytosis. For the endocytosis mechanism, the argument focus in recent years is whether the endocytosis is dependent on the dimerization, the kinase activity, the phosphorylation of the amino acid sites, the ubiquitination, and the motif of the C-terminal of the EGFR When two kinds of antibodies binding EGFR Domain III are used at the same time, the EGFR does not form the active dimer and there is no obvious phosphorylation at the tyrosine sites, which is same as the phenomenon of the EGFR when using one kind of antibody. Sorkin et al. think that: no matter the EGF having the high or low dose is used, the endocytosis of the EGFR has the great correlation with the kinase activity of the EGFR and the phosphorylation of the main tyrosine sites. It can be seen that: if the endocytosis is dependent on the phosphorylation mechanism, the endocytosis phenomenon of the antibody cannot be explained. Pier et al. think that: when the EGF having the high concentration simulates, the ubiquitination modification of the EGFR can facilitate the endocytosis thereof. There is the widespread controversy whether the ubiquitination can facilitate the endocytosis of the EGFR. When the EGF having the low concentration acts, the endocytosis of the EGFR is through the clathrin-mediated way and the ubiquitination degree is low, that is to say the endocytosis does not rely on the ubiquitination. However, when the whole intracellular domain of the EGFR lacks, the single ubiquitin molecule fused at the end of the EGFR actually helps the endocytosis of the EGFR in the way of caveolae. Data of Yosel Yarden indicate that: when two antibodies act on the EGFR, the ubiquitination modification of the EGFR happens, but the role of the ubiquitination playing in the endocytosis mechanism of the EGFR affected by the antibodies is still not clear. Zhixiang Wang et al. think that: the endocytosis of the EGFR does not rely on the kinase activity of the EGFR, but mainly relies on the phosphorylation modification of the amino acids and the most regions of the C-terminals in the intracellular domain of the EGFR. However, the above mechanism still cannot explain the endocytosis behavior of the antibody. Yosef Yarden et al. point out in 2004 that: if the anti-HER-2 Herception and the L26 monoclonal antibody are used at the same time, the endocytosis of the EGFR does not rely on the intracellular domain of the EGFR, even the transmembrane domain. When researching the endocytosis mechanism of the anti-EGFR bispecific antibody molecule having the non-overlapping epitope, Paul M. P. van Bergen en Henegouwen et al. find that: when the endocytosis of the EGFR is through the clathrin-mediated way, even if the intracellular domain part of the EGFR lacks, large amount of the internalization of the EGFR still happens and the internalization amount even exceeds the complete EGFR in the intracellular domain. However, Paul M. P. van Bergen en Henegouwen et al. also point out that: the dimerization of the N-terminal of the transmembrane domain of the EGFR is very important for the internalization of the complete EGFR. Thus, when the antibody interacts with the EGFR, the endocytosis behavior of the EGFR cannot be explained by the endocytosis mode of the EGFR when the EGF simulates. The inventors think that: when the antibody acts, the endocytosis mechanism of the EGFR is related to the special endocytosis way thereof. Espen Stang et al. find that: when both of the Cetuximab and anti-Cetuximab IgG antibodies are used, large amount of endocytosis of the EGFR happens through the way of macropinocytosis, which does not rely on the phosphorylation, but relies on the polymerization of the actin. Yosef Yarden et al. guess that: the above endocytosis behavior is related to the size of the antibody-receptor complex formed on the cell surface by the antibody. When the antibody is used, because of the non-overlapping epitope, large amount of the EGFR is passively aggregated, so that the antibody-receptor complex having the large molecular weight is formed on the cytomembrane, which cannot be caused by using one kind of antibody or using two kinds of epitope-competitive antibodies. It is shown by the mass spectrum experiment data that: two anti-HER-2 bispecific antibodies having the non-overlapping epitope can form the complex of 1716 kDa on the cytomembrane, which proves the above guess to some extent. However, the mechanism which prompts the endocytosis of the EGFR in the way of macropinocytosis is still not clear, and the endocytosis way of macropinocytosis is accompanied by the large amount of degradation of the receptor.

It is shown by some documents that: besides involving in the endocytosis, the clathrin also facilitates the intracellular cycle of the endosome and degrades without relying on the ubiquitination mechanism. The endocytosis way of macropinocytosis can greatly increase the endocytosis efficiency and the degradation efficiency.

Under the effect of the high concentration EGF, the macropinocytosis of the EGFR can still happen, and the EGFR is prompted to be aggregated on the membrane, so as to form the EGFR polymer. Compared with the complex formed through prompting the polymerization of the EGFR with using two non-competitive antibodies, the aggregation of the EGFR under the effect of EGF is an action which actively depends on the phosphorylation and the aggregation of the actin. The inventors think that: when two antibodies are used at the same time, during the passive aggregation process of the EGFR, the local flow of the cytomembrane is caused and the microfilaments are aggregated again, which facilitates the endocytosis of the EGFR in the way of macropinocytosis without relying on the motif and the modification of the intracellular domain of the EGFR. All the above researches target the endocytosis induced by the antibody of the immune globulin structure and the endocytosis mechanism thereof.

The background knowledge and the preliminary study of the immunoregulatory protein of Ganoderma lucidum are described as follows. The protein structure of the protein drug provided by the present invention is completely different from the conventional immune globulin antibody that the protein is derived from the immunoprotein of Ganoderma lucidum. In 1989, Kino et al. obtained the immunoregulatory protein of Ganoderma lucidum through separating and purifying the Ganoderma lucidum mycelium extract, and measured the amino acid sequence and the immune bioactivity thereof. The above protein is named as Lingzhi-8 (LZ-8), which consists of 110 amino acid residues with acetylated amino terminals, and has a molecular weight of 12.4 kDa and an isoelectric point of 4.4.

However, the natural LZ-8 extracted by Kino et al. contains 1.3% of polysaccharides. With the genetic engineering technology, the inventors obtain the recombinant immunoregulatory protein of Ganoderma lucidum (rLZ-8) which has the same amino acid sequence and similar activity as the natural LZ-8 and has the purity higher than 99% through the recombinant expression in the Pichia pastoris. Through the animal pharmacodynamic experiments, it is proved that: the rLZ-8 has the antitumor effect (CN 101475632). It is showed by the tumor-bearing mice experiments that: the rLZ-8 can inhibit the in vivo growth of the Ehrlich ascites carcinoma cells S180 and the transplanted liver cancer cells H22 of the mice. It is showed by the protein fluorescent labeling experiments that: the antitumor effect of the rLZ-8 is to induce the apoptosis of the cytomembrane through the specific binding with the tumor cytomembrane and therefore to wound or kill the tumor cell. It can be seen that: finding the own antitumor domain of the rLZ-8 and the target receptor on the tumor cell will bring the new technology to the cancer therapy.

The N-terminal of the LZ-8 is an important formed dimer domain, and the C-terminal is a FNIII domain. The N-terminal is folded by one α-helix (consisting of 14 amino acids with an amino acid sequence 2 SDTALIFRLAWDVK-15) (of SEQ ID NO: 1, residues 2-15; or SEQ ID NO:2) and one β-sheet (consisting of 5 amino acids with an amino acid sequence of 16 KLSFD-20) (SEQ. ID NO:1, residues 16-20), wherein the Ser residue on the α-helix is acetylated. One α-helix and one β-sheet of the N-terminal fold to form a monomer of the dimer, and the monomer interacts with another same monomer through the domain to form a dumbbell-shaped dimer. The FNIII domain of the C-terminal belongs to the sandwich structure similar as the immune globulin. The C-terminal is formed by β-plane I and β-plane II, wherein the β-plane I and the β-plane II are respectively formed by β-sheet A-B-E and β-sheet G-F-C-D.

In the research and development of the protein drugs, the computational molecular simulation also plays an important role. Firstly, through utilizing the computational molecular simulation technology, according to the crystal structure of the protein drug, the activity domain thereof can be predicted; through simulating the interaction between the protein drug and the effect target thereof (such as the interaction between the receptor and the ligand), the binding form and the binding site can be predicted, and the binding ability can be calculated. Through utilizing the computational molecular simulation software, the amino acid residue having the key binding ability or the specific location structure can be processed with mutating, so as to analyze the influence of the location change on the binding ability of the protein drug with the target and to further analyze the key domain exhibiting the activity and the key amino acid residue. Generally, the key amino acid residue is selected to be mutated to alanine (Ala) for the mutation analysis. The alanine is the most commonly used amino acid in the mutation analysis with the side chain merely having one methyl, and has the small volume and no other functional group; and meanwhile, the problem that the glycine α-C having no chirality group will greatly affect the structure is avoided. Through mutating the target amino acid into the alanine, the effect of the original amino acid on the structure and function can be analyzed. Moreover, through the computational molecular simulation technology, the original protein drug can be designed and modified. For example, through calculating and analyzing the electrostatic interaction, the electrical property modification of the amino acid at the key location is a common modification strategy. Through modifying the original amino acid generating the electrostatic repulsion into the amino acid having the inverse electrical property, the repulsive interaction between the location and the target is decreased, thereby increasing the binding ability between the protein drug and the target and obtaining the optimized protein drug. In addition, there are many other design and modification strategies, such as the spatial modification according to the structure and the side chain characteristics of the amino acid residue at the key location of the protein drug.

Another advantage of the computational simulation technology lies in that: through the molecular simulation technology, the optimization and modification of the known protein can be expected, which enables the protein to own one or more characteristics of the ideal anti-EGFR antibody. For example, the optimized and modified protein can be proved to have the outstanding activity in the antitumor mechanism with the EGFR as the target that the protein can effectively prevent or delay the tumor growth of the patients; the optimized and modified protein can be proved to have the outstanding activity in preventing or delaying the tumor growth of the patients that the protein can contend against other therapeutic drugs and therapy thereof and can be applied in the antitumor therapy alone, such as the Erlotinib, cis-platinum, adriamycin, Trastuzumab and Cetuximab. Moreover, the structure of the protein can be processed with engineering modification, so as to decrease the surface hydrophobicity thereof, to increase the industrial production (such as facilitating purification and quantitation, and increasing the thermodynamic and chemical stability, solubility and uniformity), the stability of the preparation, and the pharmacokinetic characteristics (such as decreasing the clearance rate of the non-specific binding in vivo), and to keep or increase the affinity to the EGFR. Furthermore, the optimized and modified protein can be proved to have the in vivo stability, and the good physical and chemical stability, including but not limited to the acceptable thermodynamic and chemical stability, solubility and pharmacokinetic characteristics in the tumor therapy.

SUMMARY OF THE PRESENT INVENTION

It is found that: an anti-EGFR (epidermal growth factor receptor) domain exists in a structure of rLZ-8 (recombinant immunoprotein of *Ganoderma lucidum*, a sequence thereof refers to SEQ ID NO: 1); particularly, the domain through positive potential characteristics thereof induces a killing effect to an abnormal EGFR-expressed tumor. Based on the above scientific discovery, through utilizing computational simulation technology, rLZ-8 mutants having a stronger antitumor effect are obtained.

According to the present invention, a disclosed antitumor mechanism of the rLZ-8 is that: after the rLZ-8 binds with overexpressed EGFR on a surface of cytomembrane, a violent internalization occurs in a way of macropinocytosis; the cytomembrane containing the rLZ-8 does not return back to the surface of the cytomembrane; after strongly absorbing the rLZ-8, shrinkage and rounding of the cell successively happen; and finally, a cycle of a membrane structure is blocked, causing disruption and death of the cell.

Through using inhibitors of different endocytosis ways, it is confirmed that endocytosis of the rLZ-8 is mediated by the way of macropinocytosis.

According to reported mechanism characteristics of the macropinocytosis, details and characteristics of the rLZ-8 internalization are further researched. Compared with the negative control group as filamentous actin (F-actin) having a complete structure, after the rLZ-8 simulates, a F-actin structure cannot be observed at cellular abdomen, illustrating that the F-actin participates in the internalization of the rLZ-8 and the fragmented actin after recombination participates in formation of endosome. Dextran with a high molecular weight, serving as a marker of the macropinocytosis, has an obvious co-localization phenomenon in the cell. Moreover, with the internalization of the rLZ-8, pseudopodium, shrinkage and vesicles related to the macropinocytosis can all be observed from electron microscope results.

Some reports thought that: the macropinocytosis is a cholesterol-dependent process, and an internalization efficiency of the rLZ-8 can be inhibited by 50% by a cholesterol inhibitor of mβCD. Because GTPase participates in adjusting the macropinocytosis process, the inventors researched effects thereof on the internalization of the rLZ-8. With the internalization of the rLZ-8 and bovine serum albumin (BSA), ras GTP, Arf6 GTP and Rac1 GTP are all activated; the activation caused by the BSA reverts to an original level after internalization for 1 hour; and the rLZ-8 continuously keeps a high-activity condition. In conclusion, the rLZ-8 enters the tumor cell through the internalization in the way of macropinocytosis, and the internalization way may be related to toxicity of the tumor cell.

Through a large number of researches, a relationship between the internalization of the rLZ-8 and the cell death induced thereby is disclosed by the present invention. After the rLZ-8 of 100 µg/mL acts for 5 hours, shrinkage, burst and death of Hep G2 cells happen.

Through real-time dynamic observation, it is found that: shrinkage and rounding of the cell successively occur; and finally, due to lack of the cytomembrane, the cell is disrupted and dies. In order to better show the death process of the cell, the rLZ-8 with a lower dose (10 µg/mL) is applied in following experiments. The rLZ-8 is removed after acting for 6 hours; then the cell is cultured in a normal medium; after culturing for 24 hours, red fluorescent vesicles around cell nucleus still exist, and the internalized rLZ-8 seems not to be degraded by lysosome. In comparison, the BSA is degraded merely after being cultured for 20 minutes. However, if the BSA is cultured after the rLZ-8 acts for 4 hours, the BSA does not be degraded, but has an obvious co-localization phenomenon with the rLZ-8.

According to above results, combined with respective effects of the endosome and the lysosome in the BSA degradation, related activity and cell imaging is applied in degradation researches of the internalization of the rLZ-8. After acting on the cell for 10 minutes, the rLZ-8 and Rab5 start to have a co-localization phenomenon; 30 minutes later, the co-localization phenomenon gradually disappears; then, the rLZ-8 and Rab7 start to have a co-localization phenomenon which is maintained continuously. During the whole internalization process, the rLZ-8 never has a co-localization phenomenon with Lamp1. Above results show that: the internalization of the rLZ-8 is retained at a late endosome phase and does not have a fusion with the lysosome, may leading that a large amount of the rLZ-8 is accumulated in the large endosome phase. Luzio et al. reported that: through controlling release of Ca2+, fusion between LE and the lysosome can be inhibited; then through adding enough $CaCl_2$, the fusion can be recovered. In the present research, the addition of the $CaCl_2$ does not lead to the fusion of the LE containing the rLZ-8 with the lysosome. Thus, following researches are focused on measurement of activity of Rab7 in the internalization process of the rLZ-8. Results in FIG. 15b show that: with the internalization of rLZ-8, the activity of the Rab7 is maintained in a relatively low level; in comparison, the activity of the Rab7 increases in the internalization of the BSA, illustrating that the LE containing the BSA has a fusion with the lysosome.

According to the above results, the reason why the late endosome containing the rLZ-8 does not have a fusion with the lysosome can be preliminarily deduced. More importantly, what effect will caused by the continuous accumulation of the LE to the functioning of the whole cytomembrane is studied through researching a cycle of the cytomembrane during the internalization process of the rLZ-8. Two cytomembrane markers are selected, respectively EGFR and TfR (transferrin receptor). With the endocytosis of the rLZ-8 of respectively 1 hour, 2 hours, 4 hours and 6 hours, the rLZ-8 still keeps a high-degree co-localization phenomenon with the markers. Another important phenomenon showing the abnormal retention of the late endosome is that the rLZ-8 always keeps a clear co-localization with the actin formed by the mediated macropinosome. It can be seen from the above-mentioned that: with the internalization of the rLZ-8, the cytomembrane containing the rLZ-8 does not return back to the surface of the cytomembrane. In conclusion, the blocked cycle of the cytomembrane, caused by the excessive internalization of the rLZ-8 through the macropinocytosis, may be the inducement of the cell shrinkage and death.

In the early experiments of the present invention, because the molecular weight of the rLZ-8 is merely 12.4 kDa, the rLZ-8 has a relatively short in vivo half-life period. In order to increase the in vivo half-life period and the renal clearance of the rLZ-8, through researches of the modifier of the rLZ-8, methoxy polyethylene glycol succinimidyl propionate (mPEG-SPA-rLZ-8) is constructed; and in the animal pharmacodynamic experiments, it is found that the antitumor effect of the above modifier is decreased, illustrating that the location of the modifier is greatly related to the important antitumor region of the rLZ-8. Thus, with the molecular docking technology, the location of the steric hindrance may be formed by the mPEG is calculated.

Firstly, on the basis of the crystal structure of the rLZ-8, the structure model of the mPEG-SPA-rLZ-8 is constructed, and the steric hindrance formed by the mPEG polymer is calculated through the molecular docking technology. Because the mPEG chain has a strong flexibility, the calculation quantity cannot be withstood by the common large workstation, and merely one-tenth of the extracted mPEG-SPA (with a molecular weight of 5000 Da) is calculated. Thus, the accuracy of the calculation structure is unknown. The extracted PEG16 chain is docked to a possible active site of the rLZ-8 in the Discovery Studio 2.5 through an operation method of CDODOCKER. Thereafter, all the amino acid locations may influence the rLZ-8 are processed with one or multiple site-specific mutations, and the generated mutants are processed with stability analysis of the molecular dynamics simulation through Amber. Finally, two regions, which are mostly like to be the antitumor regions of the rLZ-8 and to bind with the EGFR, are obtained. The first region is formed by $6^{th}$-$20^{th}$ amino acids; and the second region is formed by $41^{st}$-$74^{th}$ amino acids. Five amino acids having the representative locations are selected from the two regions. In order to study the effects and functions of every selected amino acid on the antitumor hotspot region, the nine amino acids are arranged and combined. Some amino acids of the nine amino acids are mutated to alanine, and then plasmids are newly constructed; the recombinant expressed mutated amino acid sequences in the *Pichia pastoris* expression system are prepared according to a purification process of the rLZ-8, and the recombinant expressed mutants are obtained. In the EGFR affinity and animal pharmacodynamic experiments with the recombinant expressed mutants, the two key regions (as shown in FIG. 1) represented by the five mutation sites are analyzed. The amino acid sequence of the rLZ-8 is showed in the attachment.

In the first region (formed by $6^{th}$-$20^{th}$ amino acids), the $9^{th}$ amino acid of arginine (R9), the $16^{th}$ amino acid of lysine (K16) and the $18^{th}$ amino acid of serine (S18) are selected as the representative amino acids. In the second region (formed by $41^{st}$-$74^{th}$ amino acids), the $41^{st}$ amino acid of lysine (K41) and the $45^{th}$ amino acid of aspartic acid (D45) are selected. Five mutants are totally obtained, respectively the rLZ-8 (K16A/S18A/K41A/D45A), the rLZ-8 (K16A/K41A), the rLZ-8 (D45A), the rLZ-8 (S18A) and the rLZ-8 (R9A).

Results of the EGFR affinity test with the five mutants show that: four mutants of the rLZ-8 (K16A/S18A/K41 A/D45A), the rLZ-8 (K16A/K41 A), the rLZ-8 (D45A) and the rLZ-8 (S18A) have the obviously decreased affinity; the rLZ-8 (K16A/S18A/K41 A/D45A) and the rLZ-8 (K16A/K41 A) nearly have no affinity with the EGFR, and the affinity constants (KD) thereof are merely $3.06\times10^{-5}$M and $1.24\times10^{-6}$ M; with changing merely one amino acid, the affinities of the rLZ-8 (D45A) and the rLZ-8 (S18A) are decreased by two orders of magnitude to $10^{-7}$ M; and, the affinity of the rLZ-8 (R9A) has no obvious change.

It is shown by the in vitro cellular activity experiments that: even the rLZ-8 has a high dose of 100 μg/mL, except the rLZ-8 (R9A), the efficiencies of the other four mutants of binding with the Hep G2 cytomembrane and entering the cell are greatly decreased; especially the rLZ-8 (K16A/S18A/K41 A/D45A) has little binding amount with the Hep G2 cytomembrane and nearly cannot be observed to enter the cell. Whether the rLZ-8 enters the cell is an important factor of tumor killing thereof, and thus it is proved that the two predicted regions are important regions for the antitumor effect of the rLZ-8 and for binding with the EGFR.

It is shown by the animal pharmacodynamic experiments of liver cancer, lung cancer, breast cancer and colon cancer that: compared with a negative control group, the groups of rLZ-8 (K16A/S18A/K41A/D45A), the rLZ-8 (K16A/K41A), the rLZ-8 (D45A) and the rLZ-8 (Si 8A) have no obvious tumor weight difference and have nearly no tumor inhibitory effect, illustrating the two predicted regions play a crucial role in the antitumor effect of the rLZ-8. After being unable to bind with the EGFR, the endocytosis and the antitumor effect thereof are greatly decreased.

It is found by comparing the alanine mutant of rLZ-8 (K16A/S18A/K41A/D45A) with the rLZ-8 that: in the rLZ-8, the surface of the region formed by the amino acids at the above four locations has the positive potential; after mutating into the alanine, the region surface becomes neutral, and the region loses the capacity of binding with the EGFR and inhibiting the tumor. Meanwhile, compared with the fungai immunomodulatory protein from flammulina velutipes (FIP-fve) which has the similar structure as the rLZ-8 and belongs to the same family, the same region at the FIP-fve has the negative potential and does not have the capacity of binding with the EGFR and inhibiting the tumor.

Thus, with the rLZ-8 mutant development strategy of increasing the positive potential of the above region or decreasing the surrounding negative potential, through the calculation of the computational simulation technology, the region and the surrounding negative potential region are processed with the site-specific mutation. The site-specific mutation locations are respectively: $6^{th}$-$9^{th}$ amino acids (6-LIFR-9), $16^{th}$-$20^{th}$ amino acids (16-KLSFD-20), $41^{st}$-$46^{th}$ amino acids (41-KVLTD-46), and $68^{th}$-$74^{th}$ amino acids (68-ESKGSQK-74). In the above locations, seven mutants are selected and processed with recombination, expression and purification, so as to verify the mutation strategy. All of the mutants including the rLZ-8 alanine mutants are processed with the same fermentation and purification process as the rLZ-8, so as to construct the plasmids and obtain the recombinant expressed purified protein.

It is verified that: after processing with one or multiple specific-site mutations, except the mutant of rLZ-8 (K41 D/K46E1K74E), the other six mutants all have the obviously increased affinity with the EGFR. Compared with the rLZ-8, the affinity equilibrium constants of the mutants of rLZ-8 (D70K) and rLZ-8 (L17K/D70K) are respectively increased by four times and six times. Because the rLZ-8 (K41D/K46E/K74E) damages the key structure of the rLZ-8, the affinity thereof is decreased.

It is shown by the animal pharmacodynamic experiments of liver cancer, lung cancer, breast cancer and colon cancer that: compared with the rLZ-8 control group, the groups of rLZ-8 (D70K) and rLZ-8 (L17K1D70K) have the obviously increased tumor inhibitory effects; the other mutants have the tumor inhibitory effects close to or slightly better than that of the rLZ-8 control group and are able to obviously or slightly prolong the survival rate of the mice to a certain extent.

Compared with the rLZ-8, the mutants obtained after the specific-site mutation with the strategy of increasing the positive potential of the two key regions or decreasing the surrounding negative potential have the obviously increased affinity with the EGFR and the obviously increased antitumor effect for the abnormal EGFR-expressed cancer.

Based on the rational design and the deep study of the rLZ-8 antitumor mechanism, the key regions for binding with the EGFR and inhibiting the tumor are processed with the specific-site mutation, and the finally obtained mutants have the antitumor effect obviously better than that of the rLZ-8.

BRIEF DESCRIPTION OF THE DRAWINGS

In FIG. 2: S: standard rLZ-8; $1^{st}$ lane: rLZ-8; $2^{nd}$ lane: rLZ-8 (K16A/S18A/K41A/D45A); $3^{rd}$ lane: rLZ-8 (K16A/K41A); $4^{th}$ lane: rLZ-8 (D45A); $5^{th}$ lane: rLZ-8 (S18A); $6^{th}$ lane: rLZ-8 (R9A); $7^{th}$ lane: rLZ-8 (D70K); $8^{th}$ lane: rLZ-8 (L17K/D70K); $9^{th}$ lane: rLZ-8 (D20H/D70K); $10^{th}$ lane: rLZ-8 (D20H); $11^{th}$ lane: rLZ-8 (L17K); $12^{th}$ lane: rLZ-8 (K41D/K46E/K74E); $13^{th}$ lane: rLZ-8 (K46E/K74E); and $14^{th}$ lane: rLZ-8 (K46E).

In FIG. 3: S: standard rLZ-8; $1^{st}$ lane: rLZ-8; $2^{nd}$ lane: rLZ-8 (K16A/S18A/K41 A/D45A); $3^{rd}$ lane: rLZ-8 (K16A/K41A); $4^{th}$ lane: rLZ-8 (D45A); $5^{th}$ lane: rLZ-8 (S18A); $6^{th}$ lane: rLZ-8 (R9A); $7^{th}$ lane: rLZ-8 (D70K); $8^{th}$ lane: rLZ-8 (L17K/D70K); $9^{th}$ lane: rLZ-8 (D20H/D70K); $10^{th}$ lane: rLZ-8 (D20H); $11^{th}$ lane: rLZ-8 (L17K), $12^{th}$ lane: rLZ-8 (K41D/K46E/K74E); $13^{th}$ lane: rLZ-8 (K46E/K74E); and $14^{th}$ lane: rLZ-8 (K46E).

In FIG. 4: S: standard rLZ-8; $1^{st}$ lane: rLZ-8; $2^{nd}$ lane: rLZ-8 (K16A/S18A/K41 A/D45A); $3^{rd}$ lane: rLZ-8 (K16A/K41 A); $4^{th}$ lane: rLZ-8 (D45A); $5^{th}$ lane: rLZ-8 (S18A); $6^{th}$ lane: rLZ-8 (R9A); $7^{th}$ lane: rLZ-8 (D70K); $8^{th}$ lane: rLZ-8 (L17K/D70K); $9^{th}$ lane: rLZ-8 (D20H/D70K); $10^{th}$ lane: rLZ-8 (D20H); $11^{th}$ lane: rLZ-8 (L17K); $12^{th}$ lane: rLZ-8 (K41D/K46E/K74E); $13^{th}$ lane: rLZ-8 (K46E/K74E); and $14^{th}$ lane: rLZ-8 (K46E).

In FIG. 5: S: standard rLZ-8; $1^{st}$ lane: rLZ-8; $2^{nd}$ lane: rLZ-8 (K16A/S18A/K41A/D45A); $3^{rd}$ lane: rLZ-8 (K16A/K41A), $4^{th}$ lane: rLZ-8 (D45A); $5^{th}$ lane: rLZ-8 (S18A); $6^{th}$ lane: rLZ-8 (R9A); $7^{th}$ lane: rLZ-8 (D70K); $8^{th}$ lane: rLZ-8 (L17K/D70K); $9^{th}$ lane: rLZ-8 (D20H/D70K); $10^{th}$ lane: rLZ-8 (D20H); $11^{th}$ lane: rLZ-8 (L17K), $12^{th}$ lane: rLZ-8 (K41 D/K46E/K74E); $13^{th}$ lane: rLZ-8 (K46E/K74E); $14^{th}$ lane: rLZ-8 (K46E); and $15^{th}$ lane: rLZ-8 (L17K).

In FIG. 6: M: marker; S: standard rLZ-8; $1^{st}$ lane: rLZ-8; $2^{nd}$ lane: rLZ-8 (K16A/S18A/K41A/D45A); $3^{rd}$ lane: rLZ-8 (K16A1K41A); $4^{th}$ lane: rLZ-8 (D45A); $5^{th}$ lane: rLZ-8 (S18A); $6^{th}$ lane: rLZ-8 (R9A); $7^{th}$ lane: rLZ-8 (D70K); and $8^{th}$ lane: rLZ-8 (L17K/D70K).

In FIG. 7: M: marker; S: standard rLZ-8; $1^{st}$ lane: rLZ-8; $2^{nd}$ lane: rLZ-8 (D20H/D70K); $3^{rd}$ lane: rLZ-8 (D20H); $4^{th}$ lane: rLZ-8 (L17K); $5^{th}$ lane: rLZ-8 (K41D/K46E/K74E); $6^{th}$ lane: rLZ-8 (K46E/K74E); $7^{th}$ lane: rLZ-8 (K46E); and $8^{th}$ lane: rLZ-8 (L17K).

In FIG. 8: M: marker; $1^{st}$ lane: standard rLZ-8; $2^{nd}$ lane: 30% mobile phase B eluting sample after cation chromatography; 3rd lane: second 60% mobile phase B eluting sample; $4^{th}$ lane: flow-through sample of cation chromatography; and $6^{th}$ lane: final purification sample.

DETAILED DESCRIPTION OF THE PREFERRED EMBODIMENT

The preferred embodiments of the present invention are merely for explaining the present invention, not for limiting the present invention in any way.

First Preferred Embodiment: Prokaryotic and Eukaryotic Expressions of Recombinant Immunoregulatory Protein of Ganoderma lucidum (rLZ-8, a Sequence Thereof Refers to SEQ ID NO: 1) and Mutants Thereof According to the first preferred embodiment, "target protein" represents "rLZ-8 and mutants thereof", and "target gene" represents "genes of rLZ-8 and mutants thereof".

Figure 1:
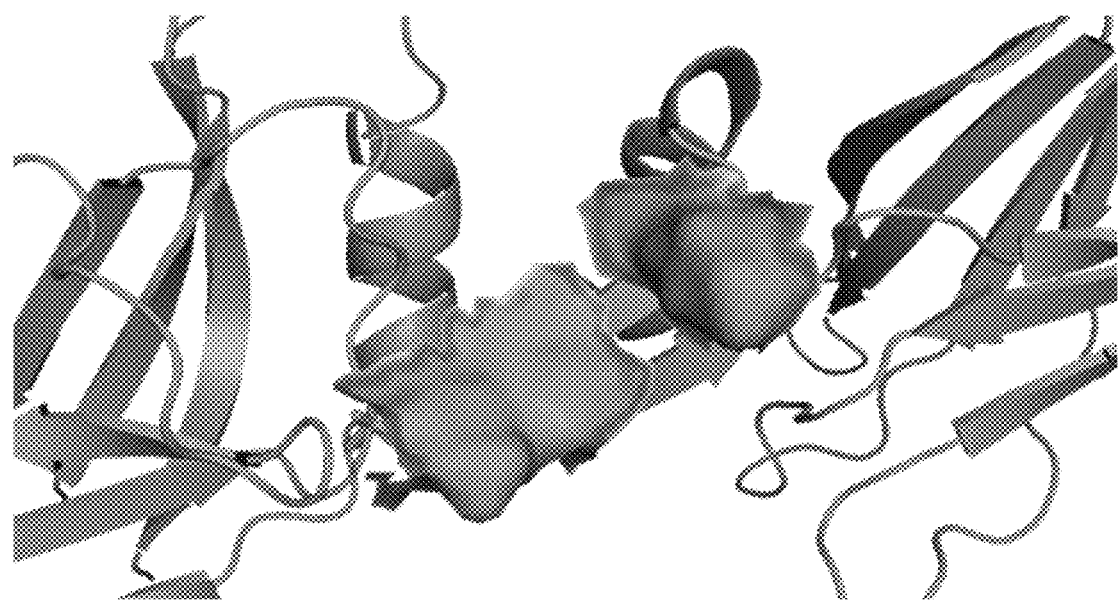
FIG. 1 is a sketch view of two key regions of recombinant immunoregulatory protein of *Ganoderma lucidum* (rLZ-8) according to the present invention.
Figure 2:
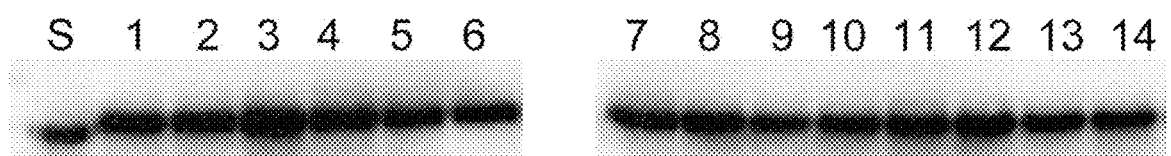
FIG. 2 shows Western blot detection results of BL21 (DE3) prokaryotic expressions of the rLZ-8 and the mutants thereof according to a first preferred embodiment of the present invention.

Construction of prokaryotic expression strain for rLZ-8 and mutants thereof and expressions of rLZ-8 and mutants thereof therein According to the first preferred embodiment, *Escherichia coli* BL21(DE3) strain which is representative in a prokaryotic expression system is adopted for expression of the target protein. Codons of the target gene are optimized; then according to a direction of a T7 promoter of a pET-28a vector, DNA sequences of Xba I restriction site and ribosome binding site are added at a 5' terminal of the target gene, termination codon and Xho I restriction site are added at a 3' terminal of the target gene, for gene synthesis. Through ligating to the pET-28a prokaryotic expression vector by the two restriction sites of Xba I and Xho I, a recombinant expression plasmid is constructed. After being validated by sequencing, the BL21(DE3) strain is transformed through heat shock, positive clones are processed with kanamycin resistance screening, and a genetic engineering strain containing the recombinant expression vector is obtained. The obtained genetic engineering strain is placed at 37° C. and cultured until OD600≈0.6; the expression of the target protein is induced at 30° C. with isopropyl-ß-D-thiogalactoside (IPTG); after collected thallus is disrupted, supernatant is collected through centrifugation for Western blot detection. Results shown in FIG. 2 indicate that the rLZ-8 and the mutants thereof provided by the present invention are expressed in the prokaryotic expression strain BL21(DE3).

Figure 3:
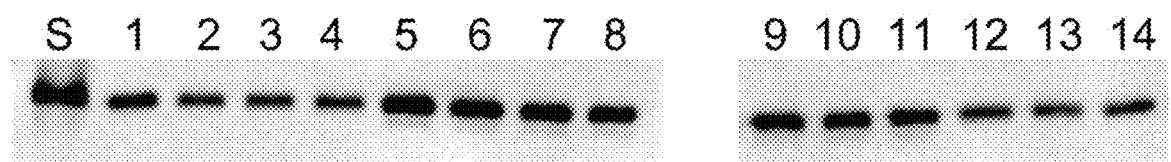
FIG. 3 shows Western blot detection results of X33 *Pichia pastoris* expressions of the rLZ-8 and the mutants thereof according to the first preferred embodiment of the present invention.

Construction of Constitutive *Pichia pastoris* Strain for rLZ-8 and Mutants Thereof and Expressions of rLZ-8 and Mutants Thereof Therein According to codon usage bias of *Pichia pastoris*, codons of the target gene are optimized; then according to a direction of a GAP promoter in a constitutive expression vector of pGAPZα A plasmid, DNA sequences of Xho I restriction site and Kex2 and Ste1 3 hydrolytic enzyme sites are added at the 5' terminal of the target gene, the termination codon and the Xba I restriction site are added at the 3' terminal of the target gene, for gene synthesis. Through the restriction enzyme ligation method, a recombinant expression vector is constructed and is sequenced for validation. According to a specification of the pGAPZα A plasmid of Invitrogen Corporation, X33 *Pichia pastoris* is electrically transformed and processed with Zeocin resistance screening, and a constitutive recombinant X33 *Pichia pastoris* expression strain for the target protein is obtained. The obtained genetic engineering strain is placed at 30° C. and cultured until OD600~6, and then is further cultured for 48 hours to enable the target protein to secrete expression; supernatant is collected through centrifugation for Western blot detection. Results shown in FIG. 3 indicate that the rLZ-8 and the mutants thereof provided by the present invention are expressed in the *Pichia pastoris* X33.

Expressions of rLZ-8 and Mutants Thereof in Mammalian Cell

Figure 4:
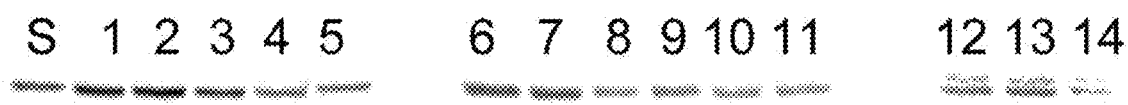
FIG. 4 shows Western blot detection results of CHO-S mammalian cell expressions of the rLZ-8 and the mutants thereof according to the first preferred embodiment of the present invention.

The expression of the target protein is made with FreeStyle™ MAX CHIO Expression System of Invitrogen Corporation. Codons of the target gene are optimized; and, Asc I and Xho I restriction sites are added for gene synthesis. Through the restriction enzyme ligation method, the target gene is transferred into a pSecTag2 A expression vector, and a recombinant target gene expression vector is obtained. Through FreeStyle™ MAX Reagent, the recombinant target protein expression vector is transfected into a CHO-S cell and then processed with hygromycin B resistance screening, so as to obtain a recombinant target protein cell strain. The obtained cell strain secretes and expresses the target protein at a condition of 37° C., 8% $CO_2$ and 135 rpm; supernatant is collected through centrifugation for Western blot detection, thereby observing the expression of the target protein. Results shown in FIG. 4 indicate that the rLZ-8 and the mutants thereof provided by the present invention are expressed in the mammalian cell of CHO-S.

Second Preferred Embodiment: Preparation of rLZ-8 and Mutants Thereof Through Fermentation Engineering Technology Construction and expression screening of the rLZ-8 and the mutants thereof are made with adopting the same expression vector and strain. According to the second preferred embodiment, *Pichia pastoris* is adopted for genome recombination and construction; the obtained strains after early shake-flask culture is screened, for screening out an engineering strain can be applied in fermentation tank scale preparation. In the following description, "target protein" represents "rLZ-8 and mutants thereof".

Detailed Process of Fermentation Technology

Working seed recovery: taking out constitutive working seeds from a refrigerator of −80° C.; slowly unfreezing at a room temperature; adding 10 μL working seeds into a 100 mL shake flask containing 10 mL YPD (yeast peptone dextrose) liquid medium; and, shake-culturing for 24 hours at a condition of 28.5° C. and 225 rpm.

Constitutive seed solution culture: keeping an OD (optical density) value of a bacteria solution of the recovered working seeds at 2-6; taking 1 mL bacteria solution, and adding into a 2 L conical flask containing 400 mL YPD medium; and, shake-culturing at a condition of 28.5° C. and 225 rpm, until the OD value of the bacteria solution is approximately equal to 6, wherein the obtained seed solution can be applied in fermentation tank culture.

Culture in Fermentation Tank:

① calibrating equipment, further comprising steps of: calibrating a pH electrode of the fermentation tank (processing pH6.86 and pH4.00 calibrations with pH calibration liquid before sterilizing the fermentation tank); calibrating a dissolved oxygen electrode (after sterilizing and cooling the medium in the fermentation tank, calibrating through stirring for more than 30 minutes with a maximum ventilation rate, an optimum temperature, an optimum pH value and a highest rotation speed of the culture condition); and calibrating a flow of a peristaltic pump;

②  preparing 3.5 L BSM (basic salt medium), and adding into a 7.5 L fermentation tank; then adding 4 mL antifoaming agent (can be sterilized) into the fermentation tank; sterilizing the medium, the fermentation tank and pipelines at a temperature of 121° C. and a high pressure for 30 minutes;

③ after sterilizing and cooling the medium in the fermentation tank, setting following parameters, wherein: temperature is set to be 29° C., rotation speed is set to be 800 rpm, ventilation rate is set to be 8 L/min and the pH value of the medium is set to be 6.0; and for sterile operation, further adding 0.22 μm filtering membrane for degerming, 8 mL Biotin and 17 mL PTM1 microelements;

④ through the sterile operation, connecting an inoculation port of the fermentation tank with a seed solution addition port; adding the above 400 mL YPD bacteria solution in the 2 L conical flask into the fermentation tank through the peristaltic pump, wherein a total volume in the fermentation tank is 3.9 L; fermenting and culturing; wherein: for the fermentation tank, a stirring speed is set to be 800 rpm, a temperature is set to be 29° C., and a DO (dissolve oxygen) value is kept at about 20%; when necessary, pure oxygen can be introduced into the fermentation tank;

⑤ taking a sample once every 6 hours; measuring OD600, a cell wet weight and a cell dry weight, and analyzing a growth situation of yeast; observing the bacterium solution by naked eyes and under a microscope; removing bacterial contaminants; and collecting supernatant;

⑥ adding PTM1 microelements into cooled 50% glycerinum after high-pressure sterilization, and uniformly mixing, wherein 12 mL microelements are added for every liter of glycerinum; and then adding the glycerinum into the medium through the peristaltic pump, wherein: during an addition process of glycerinum, the DO value cannot be lower than 20%; and an oxygen supply can be ensured through increasing the stirring speed and introducing the pure oxygen; 10

⑦ sampling strains of every time point, and processing with SDS-PAGE electrophoresis, so as to measure an expression quantity thereof; analyzing the constitutive rLZ-8, and fermenting the supernatant; and ⑧ when fermenting for 126 hours, adding 20 mL phosphoric acid into the fermentation tank, so that a certain amount of ammonium hydroxide enters the culture solution and supports fermentation as a nitrogen source; when fermenting for 150 hours, stopping culturing.

Results and Analysis

Figure 5:
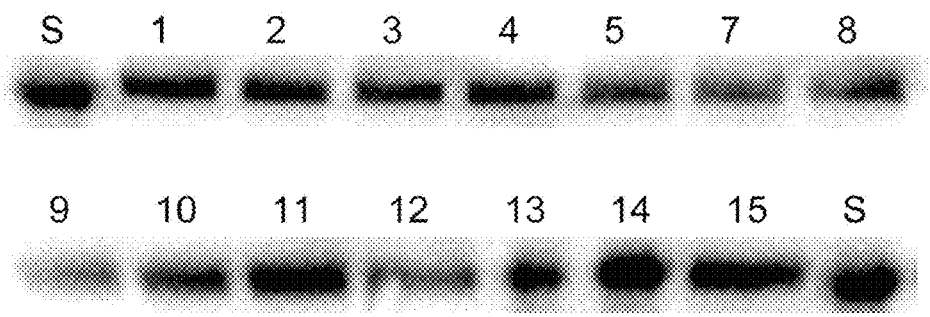
FIG. 5 shows Western blot detection results of the rLZ-8 and the mutants thereof according to a second preferred embodiment of the present invention.
Figure 6:
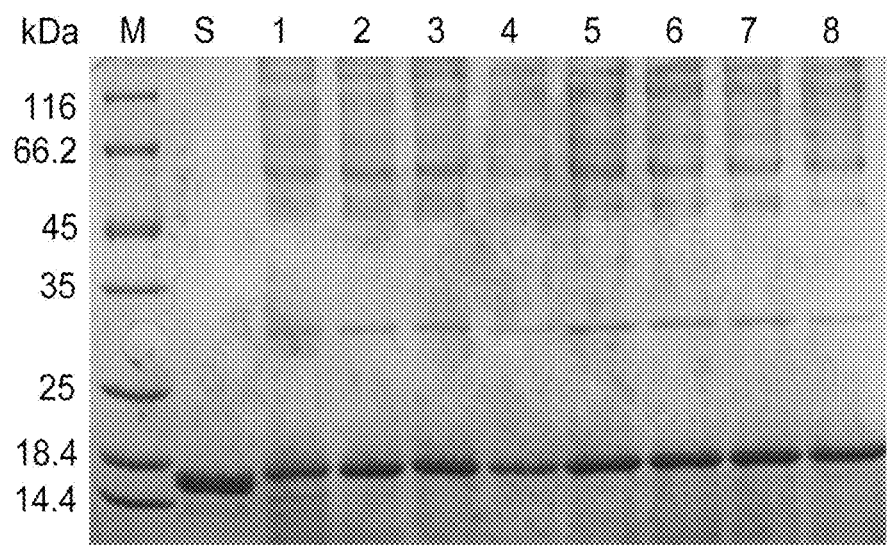
FIG. 6 shows electrophoresis detection results of the rLZ-8 and alanine mutants thereof according to the second preferred embodiment of the present invention.
Figure 7:
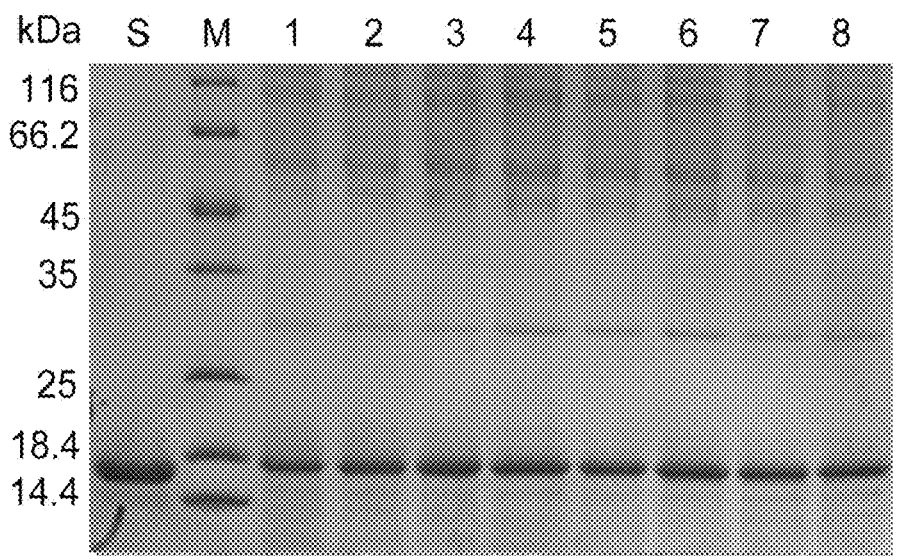
FIG. 7 shows electrophoresis detection results of the rLZ-8 and mutants thereof after surface potential optimization according to the second preferred embodiment of the present invention.

It can be seen from FIG. 5 that: according to Western Blot detection results, the rLZ-8 and the mutants thereof are all successfully prepared with a relatively high expression quantity. As shown in FIG. 6, the rLZ-8 and the alanine mutants thereof are all successively expressed, and molecular weights thereof are consistent with that of the standard rLZ-8 (S). As shown in FIG. 6 and FIG. 7, the rLZ-8 and the mutants thereof after surface potential optimization are all successfully expressed, and molecular weights thereof are consistent with that of the standard rLZ-8 (S). The marker (M) shown in FIGS. 6-7 represents the default DNA or protein fragment with the known molecular weight in the electrophoresis experiment for reference. According to the present invention, the constructed *Pichia pastoris* expression system of the constitutive protein can express the required protein without methanol induction; through adopting the glycerinum to serve as a carbon source, compared with the methanol induction, the growth rate can better meet expression requirements; moreover, growth and expression can be made at the same time, which increases the fermentation efficiency and effect.

Third Preferred Embodiment: Separation and Purification Process of rLZ-8 and Mutants Thereof 1. Experimental Methods Through many experiments, fermentation solution is successively processed with microfiltration, ultrafiltration, cation exchange chromatography and hydrophobic interaction chromatography, for separation and purification of the rLZ-8 and the mutants thereof. Because physicochemical property differences between the rLZ-8 and the rLZ-8 mutants are relatively small, a purification process of the rLZ-8 is similar as that of the rLZ-8 mutants, and the rLZ-8 mutants can be successively prepared through the purification process of the rLZ-8. However, the purification process of the rLZ-8 is not the best separation and purification process of every mutant. The third preferred embodiment does not optimize the purification process of any mutant, but merely describes the purification process of the rLZ-8 in detail as follows.

① Microfiltration Process of Fermentation Solution

Washing a well-preserved 0.7 m² hollow fiber microfiltration column with 3 L injection water, so as to remove 50 ppm sodium hypochlorite protective solution in the microfiltration column; washing the microfiltration column with 5 L 0.5M sodium hydroxide solution containing 2000 ppm sodium hypochlorite; and, measuring a pH value and an endotoxin content.

Microfiltration: measuring a conductance and a pH value of the supernatant after centrifugation, and processing with the microfiltration column, wherein: the peristaltic pump has a rotation speed of 40 rpm/min and is at first gear; and, upper and lower pressure gauges are both controlled to be ≤0.1 Mpa. After microfiltration, washing the microfiltration column with injection water; collecting column washing liquid, and mixing with the sample, wherein: an addition amount of the total volume is at least 0.25 times the volume of the original fermentation solution.

Preparing 5 L 0.5M sodium hydroxide solution containing 2000 ppm sodium hypochlorite; washing the microfiltration column with the sodium hydroxide solution; washing the microfiltration column with 10 L injection water until the pH value thereof is neutral; and preserving the microfiltration column with a certain amount of 50 ppm sodium hypochlorite.

Fermenting and centrifuging the supernatant; after microfiltration, respectively sampling for SDS electrophoresis detection; fermenting and centrifuging the supernatant, and detecting the bacterial endotoxin.

② Ultrafiltration Process of Fermentation Solution

Washing a well-preserved 0.6 m² filtering membrane with 2 L injection water, so as to remove 0.1M sodium hydroxide protective solution in the filtering membrane; washing the filtering membrane with 3 L 1M sodium hydroxide; then washing with acid liquid until the pH is neutral; measuring the pH value and a water flux.

Ultrafiltration: concentrating and desalting the sample after microfiltration by a tangential flow filtration system, wherein: a CONC-DIFI-CONC program is set and selected for concentrating; 20 L injection water is added for desalting; and according to a protein content, the sample is determined to be concentrated 5 times.

After completing ultrafiltration, a final pH value and a final conductance of the sample are measured.

Washing and preserving the filtering membrane: after processing the sample by the filtering membrane, washing the filtering membrane with 5 L 1M sodium hydroxide until reaching an original water flux and becoming neutral; and preserving the filtering membrane with 0.1M sodium hydroxide alkali liquid.

The sample after ultrafiltration is processed with SDS electrophoresis detection.

③ Cation Chromatographic Purification Process

Adding 5 L collected target protein after ultrafiltration into a mobile phase A mother solution (namely 0.02M anhydrous sodium acetate solution with pH of 3.6) of cation chromatography, and adjusting a pH value with glacial acetic acid until the pH becomes 3.6; filtering through a plate filter with a 0.22 μm filtering membrane; and preparing for sample loading.

Equilibrating chromatographic column: filling BPG (140/500) column with 1.5 L filler of Capto S; washing the column with 6 L injection water, until 20% ethyl alcohol and 0.2M sodium acetate protective solution in the column are completely removed; measuring endotoxin, wherein the chromatographic column can be used only when the endotoxin measurement result is smaller than 0.25 EU/ml; equilibrating six column volumes with the mobile phase A, wherein a flow speed is 30 L/h and an instrument protection pressure is set to be 2 bar; measuring a conductance, until the pH value and the conductance reach corresponding values of the mobile phase A.

Sample loading: loading the sample after filtration through an A3 pump, wherein a flow speed is 20 L/h; after completing loading, collecting a flow-through peak, and measuring a pH value, a conductance range and an absorption value range of 280 nm ultraviolet; eluting a non-combined peak with 8 L phase A buffer solution at a flow speed of 30 L/h, until the non-combined peak reaches an original ultraviolet absorption value; collecting the non-combined peak, and measuring a conductance range.

Eluting: according to the protection pressure, setting the flow speed, and conducting the stage eluting; washing with 12 L 10% mobile phase B (namely a solution containing 0.02M anhydrous sodium acetate and 1.5M sodium chloride with a pH value of 3.6), and then washing with 6 L 30% mobile phase B, respectively until an eluting peak reaches the original ultraviolet absorption value; collecting the eluting peaks of every stage, and measuring the conductance range and the absorption value range of 280 nm ultraviolet; taking out a certain volume of the collected eluting peak for SDS electrophoresis and high-performance liquid chromatography (HPLC) measurement; wherein: for every stage, if a purity of the eluting peak containing the target protein is lower than 50%, the eluting peak is abandoned.

④ Hydrophobic Chromatographic Purification Process

Sample processing: adding 2 L collected target protein after cation ultrafiltration into an HIC (hydrophobic interaction chromatography) phase B mother solution by volume, and adjusting a pH value with acetic acid, until the pH value becomes 5.0; then filtering through the plate filter with the 0.22 μm filtering membrane; and preparing for sample loading.

Equilibrating chromatographic column: filling the BPG (140/500) column with 1.0 L filler of Capto Phenyl; washing the column with 5 L injection water, until 20% ethyl alcohol protective solution in the column is completely removed; washing with 6 L 1M sodium hydroxide alkali liquid, and then washing with the injection water, until the pH value is neutral; processing with endotoxin detection, wherein the column can be used only when passing the detection; equilibrating eight column volumes with the mobile phase B, wherein a flow speed is 30 L/h and an instrument protection pressure is set to be 2 bar.

Sample loading: loading the sample after filtration through a sample loading pump, wherein a flow speed is 20 L/h; after completing loading, collecting a flow-through peak, and measuring a pH value and a conductance range; eluting a non-combined peak with 6 L mobile phase B buffer solution at a flow speed of 20 L/h, until the non-combined peak reaches the original ultraviolet absorption value; collecting the non-combined peak, measuring a conductance range and electrophoresis.

Eluting: setting the flow speed to be 30 L/h, and conducting the stage eluting; washing with 25 L 60% phase B, and then washing with 6 L 30% phase B, respectively until an eluting peak reaches the original ultraviolet absorption value; collecting the eluting peaks of every stage, and measuring the conductance range and the absorption value range of 280 nm ultraviolet; taking out a certain volume of the collected eluting peak for SDS electrophoresis and HPLC measurement; wherein: for every stage, if a purity of the eluting peak containing the target protein is lower than 90%, the eluting peak is abandoned.

2. Results and Analysis

Figure 8:
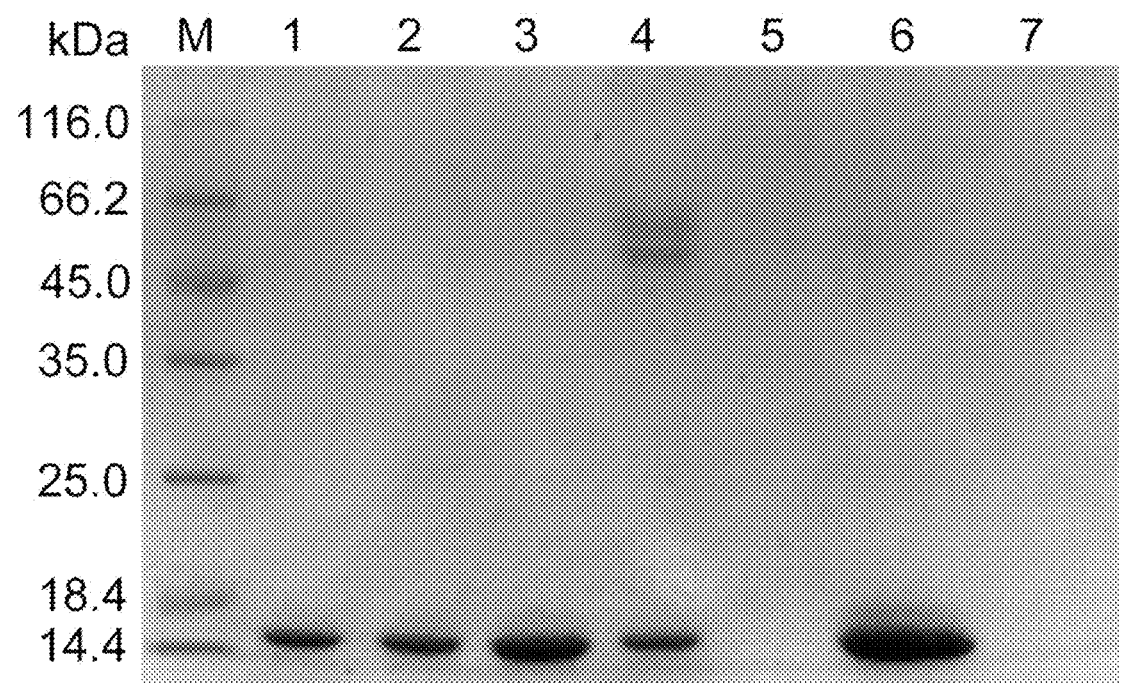
FIG. 8 shows electrophoretic detection results of samples of every stage during a purification process of the rLZ-8 according to a third preferred embodiment of the present invention.

The rLZ-8 purification results are verified as follows. The electrophoretic results shown in FIG. 8 indicate that: band locations of the 30% mobile phase B eluting sample after cation chromatography ($2^{nd}$ lane), the second 60% mobile phase B eluting sample ($3^{nd}$ lane), the first 60% mobile phase B eluting sample ($4^{th}$ lane), and the final purification sample ($6^{th}$ lane) are all consistent with the location of the obvious band of the standard rLZ-8 ($1^{st}$ lane); the 30% mobile phase B eluting sample ($2^{nd}$ lane) and the first 60% mobile phase B eluting sample ($4^{th}$ lane) still have the obvious impurity bands; the second 60% mobile phase B eluting sample (3rd lane) and the final purification sample ($6^{th}$ lane) have the obvious bands and no impurity bands, proving that the purification method is feasible. The marker (M) shown in FIG. 8 represents the default DNA or protein fragment with the known molecular weight in the electrophoresis experiment for reference.

Figure 9:
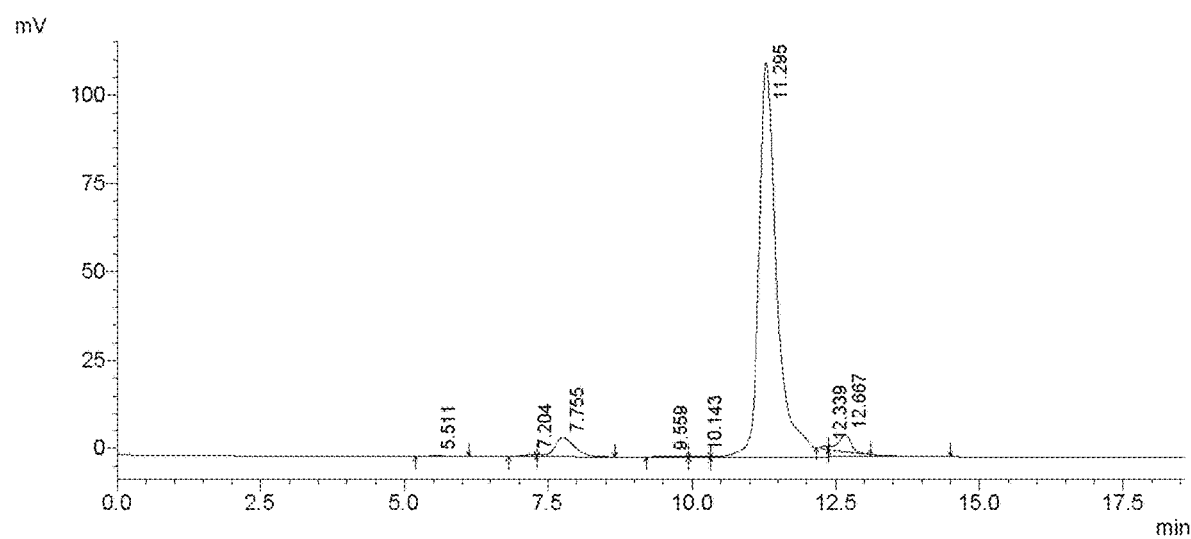
FIG. 9 shows high-performance liquid chromatography (HPLC) measurement results of the 30% mobile phase eluting sample of the rLZ-8 according to the third preferred embodiment.
Figure 10:
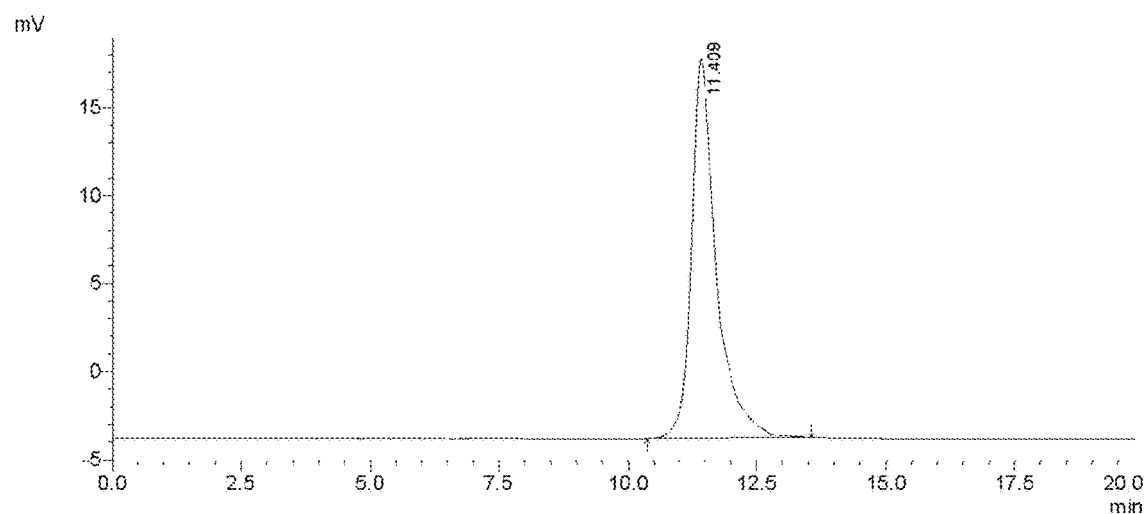
FIG. 10 shows HPLC measurement results of the 60% mobile phase eluting sample of the rLZ-8 according to the third preferred embodiment of the present invention.
Figure 11:
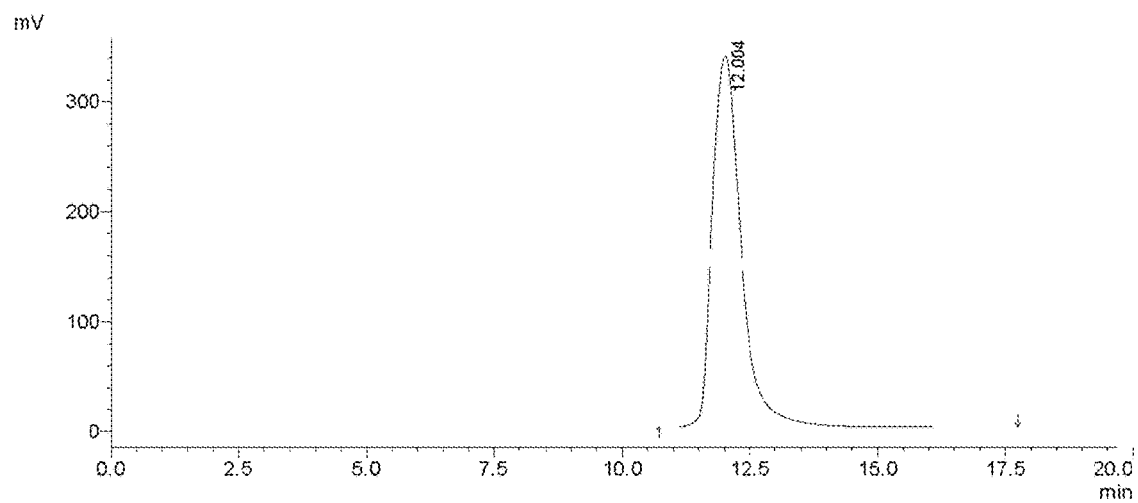
FIG. 11 shows HPLC measurement results of the final purification sample of the rLZ-8 according to the third preferred embodiment of the present invention.

The same samples are further processed with liquid phase detection. For the 30% mobile phase B eluting sample (shown in FIG. 9), the main peak (the sixth peak) has the prominent height, but about seven impurity peaks exist; through calculating according to a peak area, the purity is about 91%. As shown in FIG. 10 and FIG. 11, the second 60% mobile phase B eluting sample and the final purification sample have only one main peak with the purity of 100%, so that the liquid phase detection results are consistent with the electrophoretic results.

Fourth Preferred Embodiment: Endocytosis of rLZ-8 in Way of Macropinocytosis

1. Experimental Methods

With an ultrahigh resolution imaging system, the endocytosis way of the rLZ-8 is screened through an inhibitor experiment and a co-localization experiment.

① Endocytosis Morphology Observation of rLZ-8

The rLZ-8 is labeled by an Alexa Fluor 568 fluorescent probe; then 10 μg/mL fluorescent labeled rLZ-8 acts on Hep G2 cells for 3 hours; whether the rLZ-8 enters the cell is observed with the ultrahigh resolution imaging system; and obtained images are reconstructed, fitted and further analyzed through an image analysis software of Imaris.

② Inhibitor Screening

Inhibitors of different internalization ways are selected, respectively EIPA (macropinocytosis inhibitor), Wortmannin/LY294002 (P13K inhibitor), Nystatin+Progesterone (caveolae inhibitor) and Chlorpromazine (clathrin inhibitor); the inhibitors respectively act on the Hep G2 cells, and inhibitory effects of the inhibitors on rLZ-8 endocytosis are observed.

③ Influence of rLZ-8 Endocytosis on Microfilaments

During the macropinocytosis process, the microfilaments play an important role that can be disrupted and recombined. Thus, through observing the influence of rLZ-8 endocytosis on the microfilaments, whether the endocytosis is in the way of macropinocytosis is judged.

④ Co-Localization Research of rLZ-8 Respectively with Macropinocytosis Markers of Dextran and BSA (Bovine Serum Albumin)

Dextran and BSA are classic markers of macropinocytosis. In order to observe the endocytosis way of the rLZ-8, the rLZ-8 and the Dextran/BSA together act on the Hep G2 cells, so as to observe whether a co-localization phenomenon occurs.

2. Experimental Results

Figure 12:
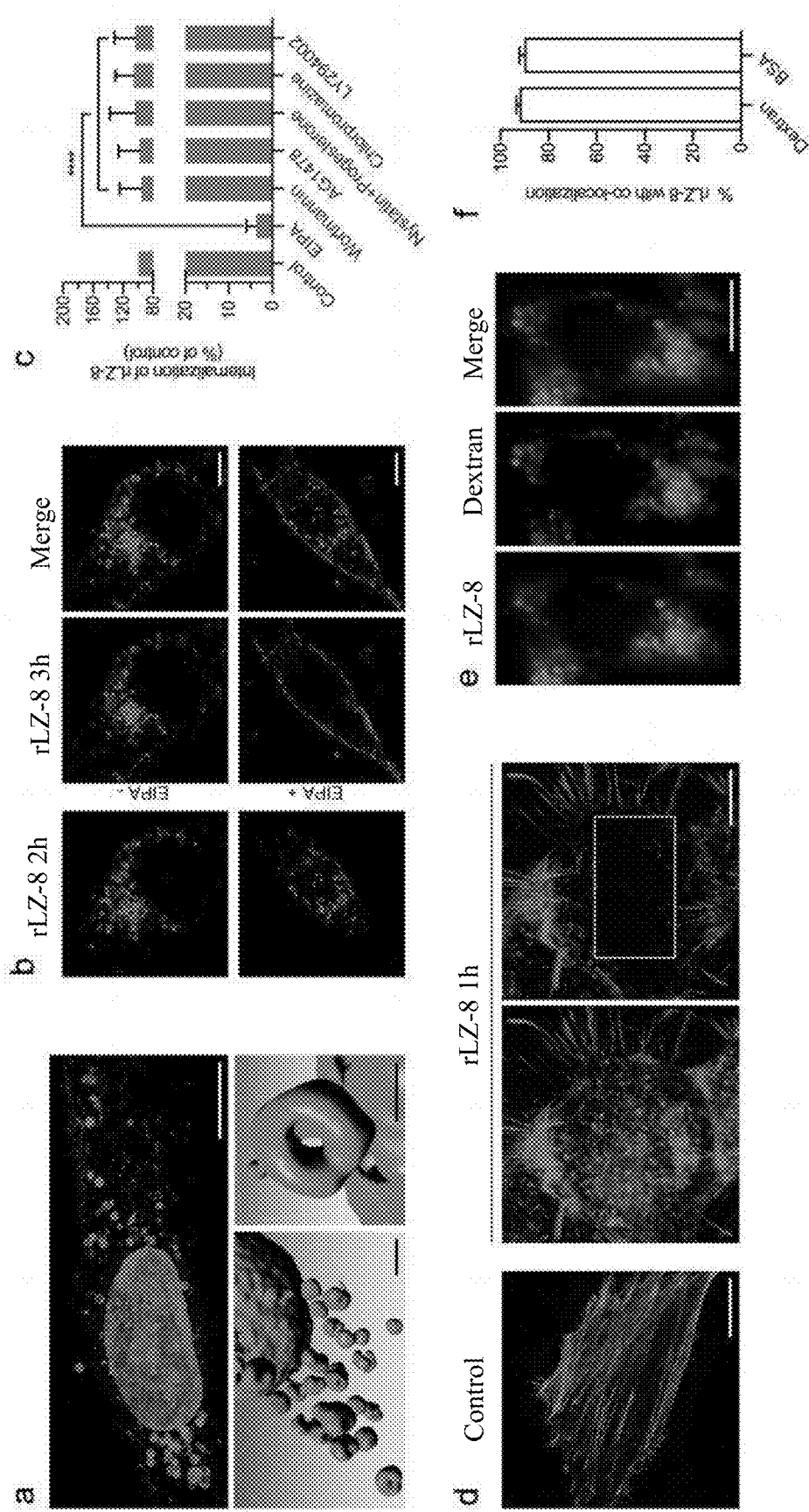
FIG. 12 shows endocytosis of the rLZ-8 in way of macropinocytosis according to a fourth preferred embodiment of the present invention

The endocytosis way of the rLZ-8 is researched according to the above methods, and results thereof are showed in FIG. 12.

It can be known from FIG. 12a that: the rL-8 is able to enter the cell through internalization and form hollow vesicles around the cell nucleus, illustrating that the rLZ-8 enters the cell in some way of internalization. It is found by the inhibitor screening (as shown in FIG. 12b and FIG. 12c) that: only the macropinocytosis inhibitor EIPA effectively inhibits the internalization of the rLZ-8, while the inhibitors of other internalization ways fail to generate the inhibitory effect, illustrating that the rLZ-8 is highly possible to enter the cell trough the way of macropinocytosis. According to characteristics of the macropinocytosis, the microfilament change during the internalization process of the rLZ-8 is observed (as shown in FIG. 12d). It is found that: during the internalization process, the microfilaments at the cellular abdomen are disrupted, illustrating that the microfilaments are involved in the internalization of the rLZ-8. Moreover, the high-degree co-localization phenomenon exists between the rlZ-8 and the classic macropinocytosis markers of Dextran and BSA (as shown in FIG. 12e). The above results indicate that the rLZ-8 enters the cell through the macropinocytosis internalization.

Fifth Preferred Embodiment: Endocytosis of rLZ-8 after Binding with EGFR (Epidermal Growth Factor Receptor)

1. Experimental Methods

Considering that the high internalization degree of the rLZ-8 may be caused by the internalization after binding with a receptor on the cytomembrane, the rLZ-8 and the receptor on the cytomembrane are screened. Relationships between the different receptors on the cytomembrane and the tLZ-8 are measured through an immunofluorescence method. Fluorescent labels are made respectively on antibodies of EGFR, c-Met, PDGFR, N-cadherin and LDLR, and co-localization situations thereof with the rLZ-8 are respectively observed.

2. Experimental Results

Figure 13:
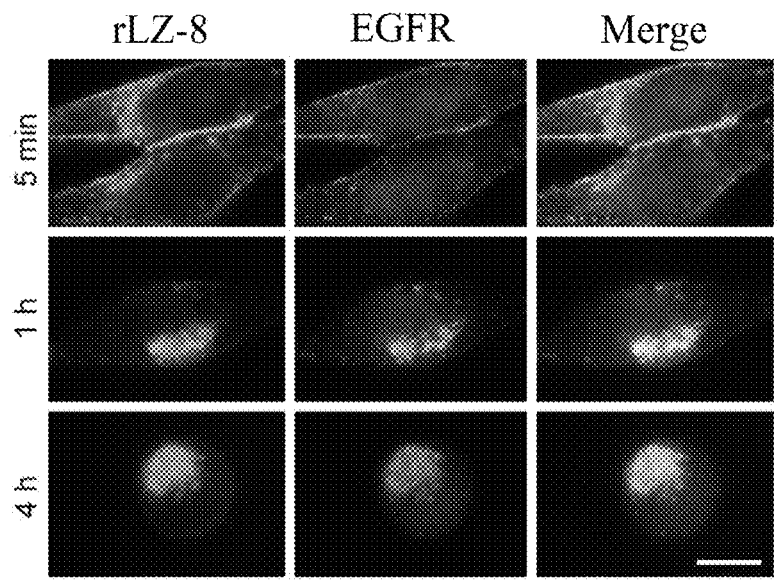
FIG. 13 shows observation results of co-localization between the rLZ-8 and EGFR (epidermal growth factor receptor) according to a fifth preferred embodiment of the present invention.
Figure 14:
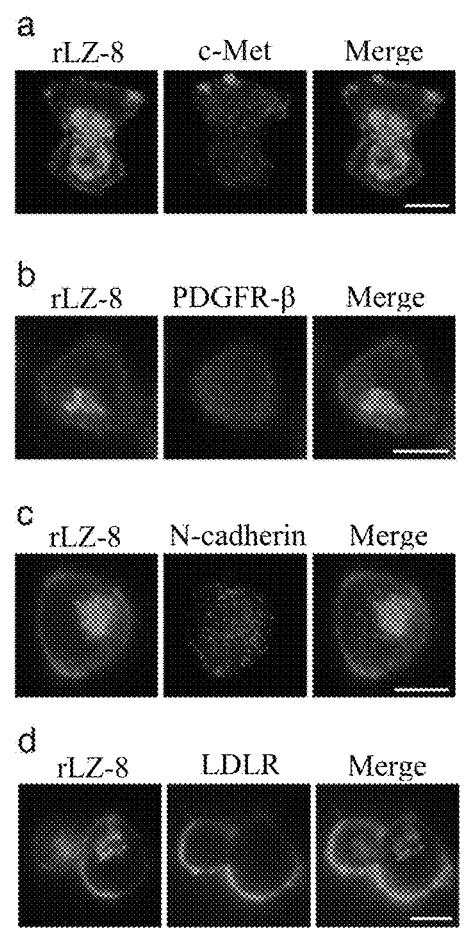
FIG. 14 shows observation results of co-localization between the rLZ-8 and other membrane receptors according to the fifth preferred embodiment of the present invention.

The immunofluorescence results are showed in FIG. 13. It can be seen from FIG. 13 that: with the internalization of the rLZ-8, a high-degree co-localization phenomenon still exists between the rLZ-8 and the EGFR. It can be seen from FIG. 14 that: no co-localization phenomenon happens between the rLZ-8 and other internalization-related membrane receptors. It is illustrated that the rLZ-8 binds with the EGFR on the cytomembrane surface and then enters the cell in the way of high-degree macropinocytosis internalization.

Sixth Preferred Embodiment: No Fusion Between rLZ-8 after Internalization and Lysosome 1. Experimental Methods During the normal macropinocytosis internalization process, the absorbed material through the early endosome and the late endosome will fuse with the lysosome and then be degraded. Thus, whether the rLZ-8 experiences the above process after internalization endocytosis is observed. Through the immunofluorescence method, Rab5 (early endosome marker), Rab7 (late endosome marker) and Lamp1 (lysosome marker) are made with fluorescent labels, and the co-localization phenomena between the markers and the rLZ-8 are observed.

2. Experimental Results

Figure 15:
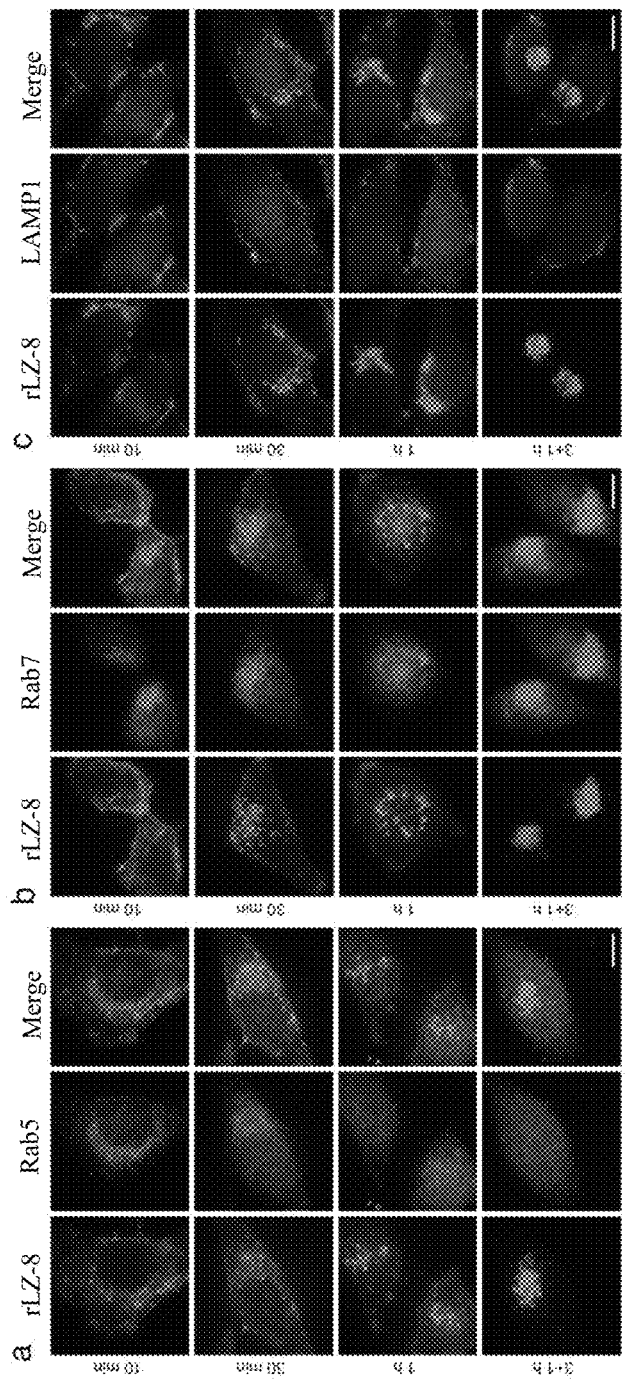
FIG. 15 shows co-localization phenomena between the rLZ-8 and Rab5, between the rLZ-8 and Rab7, and between the rLZ-8 and Lamp1 according to a sixth preferred embodiment of the present invention.
Figure 15:
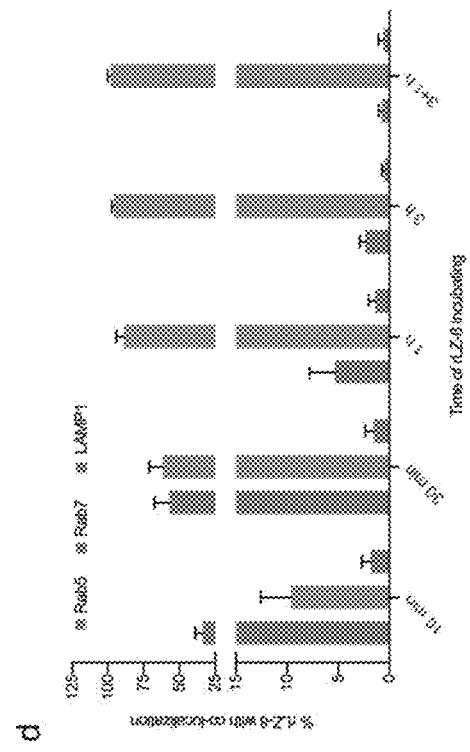

The co-localization phenomena respectively between the rLZ-8 and the Rab5, between the rLZ-8 and the Rab7, and between the rLZ-8 and the Lamp1 are showed in FIG. 15.

It can be known from FIG. 15a that: after acting on the cell for 10 minutes, the co-localization phenomenon between the rLZ-8 and the Rab5 appears, and 30 minutes later, the co-localization phenomenon gradually disappears. Followed by the disappearance of the co-localization phenomenon between the rLZ-8 and the Rab5, the co-localization phenomenon between the rLZ-8 and the Rab7 appears and is maintained (as shown in FIG. 15b). During the whole internalization process, no co-localization happens between the rLZ-8 and the Lamp1 (as shown in FIG. 15c). The above results indicate that: the internalization of the rLZ-8 is retained at the early endosome period, and the rLZ-8 does not fuse with the lysosome, which may cause the retention of the large amount of the rLZ-8 at the late endosome period.

Seventh Preferred Embodiment: Tumor Cell Death Caused by Occupation of Large Amount of Membrane after Internalization of rLZ-8

1. Experimental Methods

With the ultrahigh resolution imaging system, the whole change process of the cell after the internalization of the rLZ-8 is observed in real time; and, combined with the above researches, the reason why the rLZ-8 causes the tumor cell death is judged.

2. Experimental Results

Figure 16:
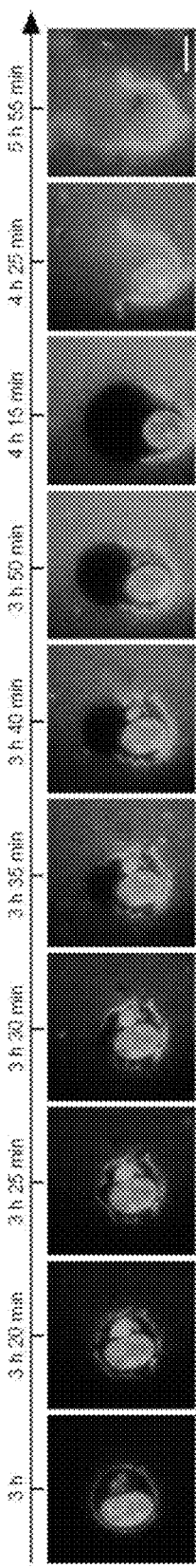
FIG. 16 shows real-time observation results of cell change after endocytosis of the rLZ-8 according to the present invention.

Real-time dynamic observation results are showed in FIG. 16. It can be known from FIG. 16 that: after the rLZ-8 acts on the cell, the shrinkage and rounding of the cell successively occur, and finally the cell is disrupted and dies. Combined with the conclusion in the sixth preferred embodiment that the rLZ-8 after endocytosis does not bind with the lysosome and is not degraded, but still fuses with the late endosome, the reason why the rLZ-8 causes the tumor cell death is analyzed as follows. When the rLZ-8 enters the cell through internalization, the cytomembrane forming the macropinosome will enter the cell with the rLZ-8; because the rLZ-8 is not degraded by the lysosome, the part of cytomembrane will not be degraded and cannot return back to the cytomembrane surface; moreover, because of the continuous high-degree internalization of the rLZ-8, more cytomembranes will be brought into the cell, causing large amount of the cytomembrane being occupied; therefore, the cell shrinkage happens, and then the cell is disrupted and dies.

If the above mechanism is correct, when the rLZ-8 stops entering the cell, the cell will not continue shrinking and dying.

Figure 17:
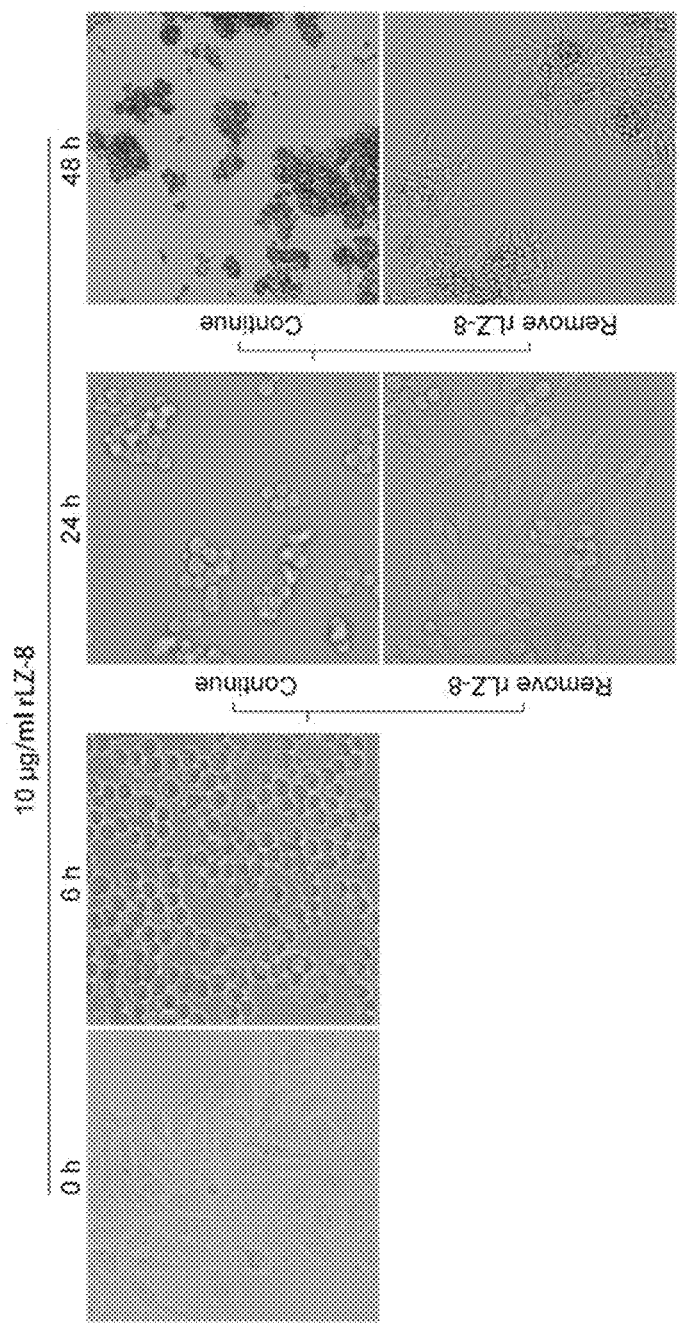
FIG. 17 shows influences of removing the rLZ-8 on cell death according to a seventh preferred embodiment of the present invention.

As shown in FIG. 17, once the rLZ-8 is removed, the internalization action stops, and the cell does not die, but grows along the cell wall and becomes normal. In conclusion, the killing mechanism of the rLZ-8 to the cell is that: through binding with the EGFR on the cytomembrane, the rLZ-8 enters the cell with the high-degree macropinocytosis internalization and is retained in the late endosome without fusing with the lysosome, so that large amount of the cytomembrane is occupied, causing the shrinkage and rounding of the cell, and finally causing the disruption and death of the cell.

Eighth Preferred Embodiment: Influences of rLZ-8 Mutants on Model Mice with Orthotopic Transplantation Tumor of Human Liver Cancer Cells 1. Experimental Methods ① Experimental Materials and Reagents NOG Mice of 6-8 weeks old are selected. The mice have a weight of 18-22 g and are bought from Beijing Vital River Laboratory Animal Technology Co., Ltd. The mice are fed under an SPF environment at Northeast Normal University; during the experiment, the temperature is controlled at (20±2) ° C., the humidity is controlled at 48%, and the mice are illuminated every 12 hours alternately. The experimental reagents comprise: human liver cancer Hep G2 cell strain, DMEM (Dulbecco's modified eagle medium), fetal bovine serum, PBS (phosphate buffer saline), pancreatin-EDTA, DMSO (dimethyl sulfoxide), 0.05% trypsin, rLZ-8, rLZ-8 mutants, and sorafenib as the positive control drug.

② Experimental Equipment and Apparatus

The experimental equipment and apparatus comprise: carbon dioxide constant-temperature incubator, full-automatic cell counting analyzer, table centrifuge, electronic scales, micropipette, culture flask, pipette, fixator, injector, scissor and tweezers.

③ Experimental Procedure

The DMEM containing 10% fetal bovine serum is selected for the human liver cancer Hep G2 cells, and then is placed in 5% $CO_2$ constant-temperature incubator at 37° C. for culturing. The Hep G2 cells at the logarithmic phase are digested by pancreatin and thereafter washed with serum-free DMEM; the living cell concentration is adjusted to 1×108 cells per milliliter, 20 µL cell suspension (with a ratio of DMEM to Matrigel™, which is solubilized basement membrane matrix secreted by Engelbreth-Holm-Swarm (EHS) mouse sarcoma cells produced by Corning Life Sciences, being 1:1) is taken and inoculated at the liver of the NOG mice, so as to construct the orthotopic transplantation tumor model of Hep G2 liver cancer cells in the NOG mice. Two weeks later, the model mice are divided into groups randomly, and each group has 10 mice. The administration method is caudal vein injection, once a day, for consecutive 28 days (qd×28, i.v.). The negative control group is injected with normal saline; the groups of the rLZ-8 and the mutants thereof are administrated with a dose of 0.5 mg/kg; the sorafenib control group is administrated with a dose of 50 mg/kg. During the experiment, if the mouse dies, the dead mouse is weighted on the same day, and the tumor tissue is taken out to be weighted. For the living mouse after administration for 28 days, the mouse is killed, and then the tumor tissue is taken out to be weighted. The death time and death number of the mice in each group are recorded in detail; the survival conditions of the mice of the experimental groups and the control groups are analyzed, and the survival rate is calculated, wherein the survival rate is obtained through subtracting the death number of the mice from the total number of the mice, and then dividing the difference by the total number of the mice.

2. Experimental Results

① Analysis of Influences of rLZ-8 Mutants on Mice Weight

After consecutive administration with caudal vein injection for 28 days, weights of the mice of the negative control group and the sorafenib control group are obviously decreased; the weights of the mice of the rLZ-8 control group have no obvious change; for the rLZ-8 mutants, compared with the weights before experiment, the weights of the mice of the groups of rLZ-8 (K16A/S18A/K41A/D45A), rLZ-8 (K16A/K41A), rLZ-8 (D45A) and rLZ-8

(S18A) are obviously decreased, while the weights of the mice of the groups of rLZ-8 (D70K) and rLZ-8 (L17K/D70K) are slightly increased. The above results indicate that: the rLZ-8 and the mutants thereof are able to adjust the physical condition of the mice; and the combinations of the sorafenib respectively with the rLZ-8 (D70K) and the rLZ-8 (1.17K/D70K) also show the relatively good effect.

Table 1 Influences of rLZ-8 Mutants on Weight of Model Mice with Tumor of Hep G2 Liver Cancer Cells

TABLE 1

Influences of rLZ-8 mutants on weight of model mice with transplantation tumor of Hep G2 liver cancer cells

| Experimental group | Mice weight before experiment (g) | Mice weight after experiment (g) |
|---|---|---|
| Negative control group | 20.4 ± 1.3 | 17.4 ± 1.8 |
| Sorafenib control group | 19.8 ± 1.0 | 19.6 ± 1.6 |
| rLZ-8 control group | 19.9 ± 0.9 | 19.8 ± 1.4 |
| rLZ-8 (K16A/S18A/K41A/D45A) | 20.2 ± 1.1 | 17.3 ± 1.5 |
| rLZ-8 (K16A/K41A) | 19.8 ± 0.8 | 17.2 ± 1.3 |
| rLZ-8 (D45A) | 70.4 ± 1.2 | 17.4 ± 1.6 |
| rLZ-8 (S18A) | 20.3 ± 1.3 | 17.6 ± 1.4 |
| rLZ-8 (R9A) | 20.1 ± 0.8 | 19.3 ± 1.3 |
| rLZ-8 (D70K) | 20.2 ± 1.2 | 20.7 ± 1.7 |
| rLZ-8 (L17K/D70K) | 20.7 ± 1.4 | 21.0 ± 1.8 |
| rLZ-8 (D20H/D70K) | 20.0 ± 1.3 | 20.1 ± 1.5 |
| rLZ-8 (D20H) | 19.5 ± 1.2 | 19.7 ± 1.7 |
| rLZ-8 (L17K) | 20.2 ± 1.3 | 20.1 ± 1.4 |
| rLZ-8 (K41D/K46E/K74E) | 20.1 ± 1.1 | 20.0 ± 1.2 |
| rLZ-8 (K46E/K74E) | 20.8 ± 1.2 | 20.1 ± 1.7 |
| rLZ-8 (K46E) | 19.7 ± 1.0 | 19.4 ± 1.8 |
| rLZ-8 (D70K) + sorafenib | 20.2 ± 1.2 | 17.4 ± 1.2 |
| rLZ-8 (L17K/D70K) + sorafenib | 20.4 ± 0.9 | 17.0 ± 0.9 |

② Influences of rLZ-8 Mutants on Tumor Weight of Mice

For the tumor weight, after weighting the stripped tumor, the mean value of the tumor weights of each group is calculated. It can be seen that: after administration for 28 days, compared with the negative control group, the groups of rLZ-8 (K16A/S18A/K41A/D45A), rLZ-8 (K16A/K41A), rLZ-8 (D45A) and rLZ-8 (S18A) have no obvious tumor weight difference and have nearly no tumor inhibitory effect; compared with the rLZ-8 control group, the groups of rLZ-8 (D70K) and the rLZ-8 (L17K/D70K) have the obviously increased tumor inhibitory effects; the other mutants have the tumor inhibitory effect nearly equal to or slightly better that that of the rLZ-8 control group. The above results indicate that: K16A/S18A/K41A/D45 is the key amino acids that influence the rLZ-8 antitumor activity: and on the rLZ-8 structure, the mutants near the above antitumor activity domain with the increased positive potential or the decreased surrounding negative potential show the better antitumor effect. The combinations of the sorafenib respectively with the rLZ-8 (D70K) and the rLZ-8 (L17K/D70K) also show the relatively good effect.

Table 2 Influences of rLZ-8 Mutants on Tumor Weight of Mice with Hep G2 Liver Cancer Transplantation Tumor

TABLE 2

Influences of rLZ-8 mutants on tumor weight of mice with Hep G2 liver cancer transplantation tumor

| Experimental group | Mice tumor weight after experiment (g) |
|---|---|
| Negative control group | 1.43 ± 0.87 |
| Sorafenib control group | 0.82 ± 0.37 |
| rLZ-8 control group | 0.62 ± 0.53 |
| rLZ-8 (K16A/S18A/K41A/D45A) | 1.62 ± 0.72 |
| rLZ-8 (K16A/K41A) | 1.46 ± 0.93 |
| rLZ-8 (D45A) | 1.44 ± 0.80 |
| rLZ-8 (S18A) | 1.50 ± 0.71 |
| rLZ-8 (M1A/R9A/D100A) | 0.78 ± 0.67 |
| rLZ-8 (R9A) | 0.65 ± 0.43 |
| rLZ-8 (D70K) | 0.35 ± 0.21 |
| rLZ-8 (L17K/D70K) | 0.42 ± 0.23 |
| rLZ-8 (D20H/D70K) | 0.51 ± 0.27 |
| rLZ-8 (D20H) | 0.60 ± 0.31 |
| rLZ-8 (L17K) | 0.58 ± 0.33 |
| rLZ-8 (K41D/K46E/K74E) | 1.25 ± 0.53 |
| rLZ-8 (K46E/K74E) | 0.69 ± 0.42 |
| rLZ-8 (K46E) | 0.75 ± 0.44 |
| rLZ-8 (D70K) + sorafenib | 0.59 ± 0.23 |
| rLZ-8 (L17K + D70K) + sorafenib | 0.52 ± 0.18 |

③ Influences of rLZ-8 Mutants on Mice Survival Rate

The experimental results indicate that: the mutants with the increased positive potential near the rLZ-8 antitumor activity domain, such as the rLZ-8 (D70K) and the rLZ-8 (L17K/D70K), have a certain effect on lengthening the survival time of the mice.

Table 3 Influences of rLZ-8 Mutants on Survival Rate of Mice with Hep G2 Liver Cancer Transplantation Tumor

TABLE 3

Influences of rLZ-8 mutants on survival rate of mice with Hep G2 liver cancer transplantation tumor

| Experimental group | Survival rate of mice after experiment (%) |
|---|---|
| Negative control group | 30 |
| Sorafenib control group | 50 |
| rLZ-8 control group | 60 |
| rLZ-8 (K16A/S18A/K41A/D45A) | 30 |
| rLZ-8 (K16A/K41A) | 20 |
| rLZ-8 (D45A) | 50 |
| rLZ-8 (S18A) | 30 |
| rLZ-8 (M1A/R9A/D100A) | 60 |
| rLZ-8 (R9A) | 50 |
| rLZ-8 (D70K) | 80 |
| rLZ-8 (L17K/D70K) | 90 |
| rLZ-8 (D20H/D70K) | 70 |
| rLZ-8 (D20H) | 60 |
| rLZ-8 (L17K) | 70 |
| rLZ-8 (K41D/K46E/K74E) | 40 |
| rLZ-8 (K46E/K74E) | 60 |
| rLZ-8 (K46E) | 60 |
| rLZ-8 (D70K) + sorafenib | 60 |
| rLZ-8 (L17K + D70K) + sorafenib | 50 |

In conclusion, compared with the rLZ-8, the mutants with the increased positive potential near the rLZ-8 antitumor activity domain, such as the rLZ-8 (D70K) and the rLZ-8 (L17K/D70K), show the better antitumor activity on the model mice with the orthotopic transplantation tumor of the human liver cancer cells, and have the certain effect on lengthening the survival time of the tumor-bearing mice. The combinations of the mutants with the sorafenib also show the relatively good effect.

Ninth Preferred Embodiment: Influences of rLZ-8 Mutants on Model Mice with Orthotopic Transplantation Tumor of Human Lung Cancer Cells 1. Experimental Methods ① Experimental Materials and Reagents The human lung cancer A549 cell strain is selected. The NOG Mice of 6-8 weeks old are selected. The mice have a weight of 18-22 g and are bought from Beijing Vital River Laboratory Animal Technology Co., Ltd. The mice are fed under the SPF environment at Northeast Normal University; during the experiment, the temperature is controlled at (20±2) ° C., the humidity is controlled at 48%, and the mice are illuminated every 12 hours alternately. The experimental reagents comprise: DMEM, fetal bovine serum, PBS, pancreatin-EDTA, DMSO, 0.05% trypsin, rLZ-8, and rLZ-8 mutants.

② Experimental Equipment and Apparatus

The experimental equipment and apparatus comprise: carbon dioxide constant-temperature incubator, full-automatic cell counting analyzer, table centrifuge, electronic scales, micropipette, culture flask, pipette, fixator, injector, scissor and tweezers.

③ Grouping and Administration

The DMEM containing 10% fetal bovine serum is selected for the human lung cancer A549 cells, and then is placed in the $CO_2$ constant-temperature incubator at 37° C. for culturing. The A549 cells at the logarithmic phase are digested by pancreatin and thereafter washed with serum-free DMEM; the living cell concentration is adjusted to 1×108 cells per milliliter; 20 μL cell suspension is taken and inoculated at the lung of the NOG mice; two weeks later, the orthotopic transplantation tumor model of A549 lung cancer cells is constructed in the NOG mice.

2. Experimental Results

① Analysis of Influences of rLZ-8 Mutants on Mice Weight

The rLZ-8 and the mutants thereof are able to adjust the physical condition of the model mice with the A549 lung cancer transplantation tumor, wherein: the mutants with the increased positive potential near the rLZ-8 antitumor activity domain have the certain positive adjustment effect on the increase of the mice weight.

Table 4 Influences of rLZ-8 Mutants on Weight of Model Mice with A549 Lung Cancer Transplantation Tumor

TABLE 4

Influences of rLZ-8 mutants on weight of model mice with A549 lung cancer transplantation tumor

| Experimental group | Mice weight before experiment (g) | Mice weight after experiment (g) |
|---|---|---|
| Negative control group | 21.4 ± 1.4 | 17.5 ± 1.8 |
| rLZ-8 control group | 21.0 ± 1.1 | 20.8 ± 1.5 |
| rLZ-8 (K16A/S18A/K41A/D45A) | 20.2 ± 1.2 | 17.6 ± 1.4 |
| rLZ-8 (K16A/K41A) | 19.9 ± 0.8 | 17.4 ± 1.5 |
| rLZ-8 (D45A) | 20.2 ± 1.1 | 17.5 ± 1.5 |
| rLZ-8 (S18A) | 20.5 ± 1.3 | 17.8 ± 1.6 |
| rLZ-8 (R9A) | 20.2 ± 0.7 | 20.0 ± 1.4 |
| rLZ-8 (D70K) | 20.0 ± 1.2 | 21.1 ± 1.2 |
| rLZ-8 (L17K/D70K) | 20.1 ± 1.4 | 21.2 ± 1.5 |
| rLZ-8 (D20H/D70K) | 20.0 ± 1.5 | 20.6 ± 1.7 |
| rLZ-8 (D20H) | 19.7 ± 1.3 | 19.9 ± 1.7 |
| rLZ-8 (L17K) | 20.1 ± 1.2 | 20.1 ± 1.4 |
| rLZ-8 (K41D/K46E/K74E) | 20.7 ± 1.3 | 19.1 ± 1.3 |
| rLZ-8 (K46E/K74E) | 20.3 ± 1.0 | 20.0 ± 1.5 |
| rLZ-8 (K46E) | 20.7 ± 1.3 | 20.4 ± 1.6 |

② Influences of rLZ-8 Mutants on Mice Tumor Weight

It can be seen that: after administration for 28 days, compared with the negative control group, the groups of rLZ-8 (K16A/S18A/K41A/D45A), rLZ-8 (K16A/K41A), rLZ-8 (D45A) and rLZ-8 (S18A) have no obvious tumor weight difference and have nearly no tumor inhibitory effect; compared with the rLZ-8 control group, the groups of rLZ-8 (D70K) and rLZ-8 (L17K/D70K) have the obviously increased tumor inhibitory effect; the other mutants have the tumor inhibitory effect nearly equal to or slightly better than that of the rLZ-8 control group.

Table 5 Influences of rLZ-8 Mutants on Tumor Weight of Model Mice with A549 Lung Cancer Transplantation Tumor

TABLE 5

Influences of rLZ-8 mutants on tumor weight of model mice with A549 lung cancer transplantation tumor

| Experimental group | Mice tumor weight after experiment (g) |
|---|---|
| Negative control group | 1.23 ± 0.74 |
| rLZ-8 control group | 0.60 ± 0.45 |
| rLZ-8 (K16A/S18A/K41A/D45A) | 1.22 ± 0.83 |
| rLZ-8 (K16A/K41A) | 1.26 ± 0.77 |
| rLZ-8 (D45A) | 1.28 ± 0.68 |
| rLZ-8 (S18A) | 1.20 ± 0.70 |
| rLZ-8 (R9A) | 0.69 ± 0.53 |
| rLZ-8 (D70K) | 0.36 ± 0.28 |
| rLZ-8 (L17K/D70K) | 0.40 ± 0.26 |
| rLZ-8 (D20H/D70K) | 0.49 ± 0.28 |
| rLZ-8 (D20H) | 0.51 ± 0.32 |
| rLZ-8 (L17K) | 0.53 ± 0.30 |
| rLZ-8 (K41D/K46E/K74E) | 1.20 ± 0.62 |
| rLZ-8 (K46E/K74E) | 0.63 ± 0.41 |
| rLZ-8 (K46E) | 0.65 ± 0.31 |

③ Influences of rLZ-8 Mutants on Mice Survival Rate

Compared with the rLZ-8, the mutants with the increased positive potential near the rLZ-8 antitumor activity domain, such as the rLZ-8 (D70K) and the rLZ-8 (L17K/D70K), can obviously lengthen the survival time of the model mice with the A549 lung cancer transplantation tumor.

Table 6 Influences of rLZ-8 Mutants on Survival Rate of Model Mice with A549 Lung Cancer Transplantation Tumor

TABLE 6

Influences of rLZ-8 mutants on survival rate of model mice with A549 lung cancer transplantation tumor

| Experimental group | Mice survival rate after experiment (%) |
| --- | --- |
| Negative control group | 20 |
| rLZ-8 control group | 50 |
| rLZ-8 (K16A/S18A/K41A/D45A) | 10 |
| rLZ-8 (K16A/K41A) | 20 |
| rLZ-8 (D45A) | 30 |
| rLZ-8 (S18A) | 30 |
| rLZ-8 (R9A) | 50 |
| rLZ-8 (D70K) | 80 |
| rLZ-8 (L17K/D70K) | 80 |
| rLZ-8 (D20H/D70K) | 70 |
| rLZ-8 (D20H) | 70 |
| rLZ-8 (L17K) | 70 |
| rLZ-8 (K41D/K46E/K74E) | 40 |
| rLZ-8 (K46E/K74E) | 50 |
| rLZ-8 (K46E) | 40 |

Tenth Preferred Embodiment: Influences of rLZ-8 Mutants on Model Mice with Orthotopic Transplantation Tumor of Human Breast Cancer Cells 1. Experimental Methods ① Experimental Materials and Reagents The experimental materials and reagents comprise: human breast cancer MCF7 cell strain, 17β estradiol sustained release tablet, BALB/c female nude mice, DMEM, fetal bovine serum, PBS, pancreatin-EDTA, DMSO, 0.05% trypsin, rLZ-8, and rLZ-8 mutants.

② Experimental Equipment and Apparatus

The experimental equipment and apparatus comprise: carbon dioxide constant-temperature incubator, full-automatic cell counting analyzer, table centrifuge, electronic scales, micropipette, culture flask, pipette, fixator, injector, scissor and tweezers.

③ Grouping and Administration

The DMEM containing 10% fetal bovine serum is selected for the human breast cancer MCF7 cells, and then is placed in the $CO_2$ constant-temperature incubator at 37° C. for culturing. One day before the experiment, 0.5 mg of 17ß estradiol sustained release tablet is embedded below the neck skin of the BALB/c nude mice. The MCF7 cells at the logarithmic phase are digested by pancreatin and thereafter washed with serum-free DMEM; 5×106 MCF7 cells are inoculated in the left second breast of the BALB/c nude mice, so as to construct the orthotopic transplantation tumor model of MCF7 breast cancer cells in the BALB/c nude mice.

2. Experimental Results

After administration for 28 days, compared with the negative control group, the groups of rLZ-8 (K16A/S18A/K41A/D45A), rLZ-8 (K16A/K41A), rLZ-8 (D45A) and rLZ-8 (S18A) have no obvious tumor weight difference and have nearly no tumor inhibitory effect; compared with the rLZ-8 control group, the groups of rLZ-8 (D70K) and rLZ-8 (L17K/D70K) have the obviously increased tumor inhibitory effect.

Table 7 Influences of rLZ-8 Mutants on Tumor Weight of Model Mice with MCF7 Breast Cancer Transplantation Tumor

TABLE 7

Influences of rLZ-8 mutants on tumor weight of model mice with MCF7 breast cancer transplantation tumor

| Experimental group | Mice tumor weight after experiment (g) |
| --- | --- |
| Negative control group | 1.03 ± 0.24 |
| rLZ-8 control group | 0.74 ± 0.35 |
| rLZ-8 (K16A/S18A/K41A/D45A) | 1.02 ± 0.33 |
| rLZ-8 (K16A/K41A) | 1.12 ± 0.37 |
| rLZ-8 (D45A) | 1.08 ± 0.28 |
| rLZ-8 (S18A) | 1.04 ± 0.30 |
| rLZ-8 (M1A/R9A/D100A) | 0.77 ± 0.32 |
| rLZ-8 (R9A) | 0.79 ± 0.31 |
| rLZ-8 (D70K) | 0.52 ± 0.28 |
| rLZ-8 (L17K/D70K) | 0.49 ± 0.26 |
| rLZ-8 (D20H/D70K) | 0.60 ± 0.27 |
| rLZ-8 (D20H) | 0.61 ± 0.22 |
| rLZ-8 (L17K) | 0.63 ± 0.31 |
| rLZ-8 (K41D/K46E/K74E) | 1.10 ± 0.42 |
| rLZ-8 (K46E/K74E) | 0.73 ± 0.24 |
| rLZ-8 (K46E) | 0.75 ± 0.32 |

Eleventh Preferred Embodiment: Influences of rLZ-8 Mutants on Model Mice with Orthotopic Transplantation Tumor of Human Colon Cancer Cells 1. Experimental Methods ① Experimental Materials and Reagents The experimental materials and reagents comprise: human colon cancer SW480 cell strain, BALB/c female nude mice, RPMI1630 medium, DMEM, fetal bovine serum, PBS, pancreatin-EDTA, DMSO, 0.05% trypsin, rLZ-8, and rLZ-8 mutants.

② Experimental Equipment and Apparatus

The experimental equipment and apparatus comprise: carbon dioxide constant-temperature incubator, full-automatic cell counting analyzer, table centrifuge, electronic scales, micropipette, culture flask, pipette, fixator, injector, scissor and tweezers.

(3) Grouping and Administration

The RPMI1640 medium containing 10% fetal bovine serum is selected for the human colon cancer SW480 cells, and then is placed in the $CO_2$ constant-temperature incubator at 37° C. for culturing. The SW480 cells at the logarithmic phase are digested by pancreatin and thereafter washed with serum-free RPMI1640 medium; 2×106 cells are inoculated below the back skin of the BALB/c nude mice; after the tumor blocks for observation are formed and have the diameter larger than 0.5 cm, the mice are divided into groups randomly; and the transplantation tumor model of human colon cancer SW480 cells are constructed in the BALB/c nude mice.

2. Experimental Results

After administration for 28 days, compared with the negative control group, the groups of rLZ-8 (K16A/S18A/K41A/D45A), rLZ-8 (K16A/K41A), rLZ-8 (D45A) and rLZ-8 (S18A) have no obvious tumor weight difference and have nearly no tumor inhibitory effect; compared with the rLZ-8 control group, the groups of rLZ-8 (D70K) and rLZ-8 (L17K/D70K) have the obviously increased tumor inhibitory effect.

Table 8 Influences of rLZ-8 Mutants on Tumor Weight of Model Mice with SW480 Colon Cancer Transplantation Tumor

TABLE 8

Influences of rLZ-8 mutants on tumor weight of model mice with SW480 colon cancer transplantation tumor

| Experimental group | Mice tumor weight after experiment (g) |
| --- | --- |
| Negative control group | 3.13 ± 0.64 |
| rLZ-8 control group | 1.94 ± 0.43 |
| rLZ-8 (K16A/S18A/K41A/D45A) | 3.12 ± 0.54 |
| rLZ-8 (K16A/K41A) | 3.12 ± 0.47 |
| rLZ-8 (D45A) | 3.26 ± 0.56 |
| rLZ-8 (S18A) | 3.01 ± 0.39 |
| rLZ-8 (M1A/R9A/D100A) | 1.97 ± 0.35 |
| rLZ-8 (R9A) | 1.89 ± 0.37 |
| rLZ-8 (D70K) | 1.22 ± 0.29 |
| rLZ-8 (L17K/D70K) | 1.09 ± 0.33 |
| rLZ-8 (D20H/D70K) | 1.60 ± 0.29 |
| rLZ-8 (D20H) | 1.54 ± 0.45 |
| rLZ-8 (L17K) | 1.62 ± 0.41 |
| rLZ-8 (K41D/K46E/K74E) | 3.10 ± 0.48 |
| rLZ-8 (K46E/K74E) | 2.23 ± 0.54 |
| rLZ-8 (K46E) | 2.15 ± 0.62 |

Twelfth Preferred Embodiment: Affinity Test Experiment

1. Experimental Methods

The Biacore™ T200 equipment (a Surface Plasmon Resonance from GE Company) is selected. Through the surface plasma resonance technology, the affinity of the rLZ-8 and the mutants thereof to the EGFR extracellular domain is tested. The CM5 chip is adopted to serve as the affinity test chip.

(1) pH Screening for Coupling

The EGFR extracellular domain (with an amino acid sequence of 25-645) serves as the ligand for coupling; 1 mg EGFR freeze-dried powders are diluted with HEPES buffer solution to a concentration of 400 μg/mL and set aside. Three 1.5 mL EP tubes are prepared; 10 μL ligand are respectively added into the three tubes, then 90 μL 10 mM sodium acetate with different pH values of 4.5, 5.0 and 5.5 are respectively added into the tubes and are mixed completely and uniformly; and a final concentration of the ligand is 40 μg/mL. Moreover, 200 μL 50 mM sodium acetate is added into another 1.5 mL EP tube. Results show that the condition of pH 5.0 is selected for ligand coupling.

(2) Ligand Coupling

The ligand has a molecular weight of 70 kDa, the analyte (rLZ-8) has a molecular weight of 12.4 kDa. In theory, one rLZ-8 antibody can bind with one EGFR, and thus the stoichiometric ratio Sm is equal to 1. Through the following equations, the coupling amount RL of the ligand is calculated.

$$R_{max} = \frac{\text{Analyte MW}}{\text{Ligand MW}} \times R_L \times S_m$$

$$100 RU = \frac{12.4}{70} \times R_L \times 1$$

$$R_L = 564.5$$

Through the experimental experience, the optimal reagent coupling amount is set to be 3*RL, and the coupling amount is set to be 1700 RU. The EGFR extracellular domain is successively coupled on the CM5 chip.

(3) Preparation of Sample to be Tested

In the affinity test, in order to eliminate the influence of different concentrations on the affinity, every of the rLZ-8 and the mutants thereof are tested with eight concentrations, wherein: seven concentrations are gradient concentrations, and the last one is the test reference concentration. Detailed concentrations are showed in Table 9.

TABLE 9

Gradient concentrations of sample to be tested

| Sample number | Sample concentration |
| --- | --- |
| C1 | 256 nM |
| C2 | 128 nM |
| C3 | 64 nM |
| C4 | 32 nM |
| C5 | 16 nM |
| C6 | 8 nM |
| C7 | 4 nM |
| C8 (reference) | 128 nM |

2. Experimental Results

After fitting and calculating the result curves, the affinity results of the tested rLZ-8 and the mutants thereof are showed in Table 10.

TABLE 10

Affinity of rLZ-8 and mutants thereof

| Name | $K_a$ (M·s$^{-1}$) | $K_d$ (s$^{-1}$) | $K_D$ (M) |
|---|---|---|---|
| rLZ-8 | 6.34 × 10$^4$ | 5.83 × 10$^{-4}$ | 9.20 × 10$^{-9}$ |
| rLZ-8 (K16A/S18A/K41A/D45A) | 1.39 × 10$^2$ | 4.23 × 10$^{-3}$ | 3.06 × 10$^{-5}$ |
| rLZ-8 (K16A/K41A) | 2.20 × 10$^2$ | 2.73 × 10$^{-4}$ | 1.24 × 10$^{-6}$ |
| rLZ-8 (D45A) | 1.20 × 10$^3$ | 7.43 × 10$^{-4}$ | 6.20 × 10$^{-7}$ |
| rLZ-8 (S18A) | 3.72 × 10$^3$ | 1.82 × 10$^{-3}$ | 4.89 × 10$^{-7}$ |
| rLZ-8 (R9A) | 6.12 × 10$^4$ | 5.28 × 10$^{-4}$ | 8.63 × 10$^{-9}$ |
| rLZ-8 (D70K) | 2.03 × 10$^5$ | 4.57 × 10$^{-4}$ | 2.25 × 10$^{-9}$ |
| rLZ-8 (L17K/D70K) | 2.15 × 10$^5$ | 3.29 × 10$^{-4}$ | 1.53 × 10$^{-9}$ |
| rLZ-8 (D20H/E68K) | 1.29 × 10$^4$ | 8.29 × 10$^{-5}$ | 6.43 × 10$^{-9}$ |
| rLZ-8 (D20H) | 5.87 × 10$^4$ | 4.32 × 10$^{-4}$ | 7.36 × 10$^{-9}$ |
| rLZ-8 (L17K) | 1.01 × 10$^4$ | 7.56 × 10$^{-5}$ | 7.49 × 10$^{-9}$ |
| rLZ-8 (K41D/K46E/K74E) | 3.53 × 10$^4$ | 4.31 × 10$^{-4}$ | 1.22 × 10$^{-8}$ |
| rLZ-8 (K46E/K74E) | 6.57 × 10$^4$ | 6.14 × 10$^{-4}$ | 9.35 × 10$^{-9}$ |

Affinities of the rLZ-8 and twelve mutants thereof are tested. Results show that: for the alanine recessive mutants at the key antitumor domain, respectively the rLZ-8 (K16A/S18A/K41A/D45A), rLZ-8 (K16A/K41A), rLZ-8 (D45A) and rLZ-8 (S18A), the affinity is obviously decreased by 2-3 orders of magnitudes.

Through calculating the potential at the protein surface, some representative mutation locations (such as the 70$^{th}$ amino acid and the 20$^{th}$ amino acid) are selected, and the amino acids which are highly likely to increase the surface positive potential are processed with mutation. Results show that: the affinities of the mutants of rLZ-8 (D70K), the rLZ-8 (L17K/D70K) and the rLZ-8 (D20H/E68K) are respectively increased by 2.3 times, 6 times and 1.4 times.

Thirteenth Preferred Embodiment: Formulations of Freeze-Dried Powders of rLZ-8 and Mutants Thereof 1. Experimental Methods American VirTis Wizard 2.0 freeze dryer is selected for exploring and determining the freeze-drying prescription and process of the rLZ-8 and the mutants thereof.

① Freeze-Drying Prescription of rLZ-8 and Mutants Thereof

Through the single factor experiment, the stabilizer and the surfactant which affect the formulation of the freeze-drying prescription are observed, and the influences of adding different ingredients on the content, purity, insoluble particles and activity of the protein are determined. A weight ratio of the main active material and the stabilizer is 1:5, and a weight ratio of the main active material and the surfactant is 20:1.

Through screening of the combined prescription, the optimal freeze-drying prescription is determined, and the basic prescription designs are showed as follows.

TABLE 1

Prescription designs of rLZ-8 and mutants thereof

| Prescription number | Mycose (mg) | Mannitol (mg) | Lactose (mg) | Twain 80 (mg) | Poloxamer 188 (mg) | rLZ-8 (mg) |
|---|---|---|---|---|---|---|
| 1 | 50 | 50 | | | | 10 |
| 2 | 50 | | 50 | | | 10 |
| 3 | | 50 | 50 | | | 10 |
| 4 | 50 | 50 | | 0.5 | | 10 |
| 5 | 50 | | 50 | 0.5 | | 10 |
| 6 | | 50 | 50 | 0.5 | | 10 |
| 7 | 50 | 50 | | | 0.5 | 10 |
| 8 | 50 | | 50 | | 0.5 | 10 |
| 9 | | 50 | 50 | | 0.5 | 10 |

② Freeze-Drying Process of rLZ-8 and Mutants Thereof

During the freeze-drying process, six sublimation drying temperatures of −23° C., −25° C., −27° C., −29° C., −31° C. and 33° C. are selected; six vacuum degrees of 100 mTorr, 150 mTorr, 200 mTorr, 250 mTorr, 300 mTorr and 350 mTorr are selected; six freeze-drying times of 50 hours, 60 hours, 70 hours, 80 hours, 90 hours and 100 hours are selected; and the single factor experiments are respectively conducted with the character as the evaluation index. Six vacuum drying temperatures of 25° C., 30° C., 35° C., 40° C., 45° C. and 50° C. are selected; six drying times of 15 hours, 20 hours, 25 hours, 30 hours, hours and 40 hours are selected; six vacuum degrees of 100 mTorr, 150 mTorr, 200 mTorr, 250 mTorr, 300 mTorr and 350 mTorr are selected; and the single factor experiments are respectively conducted with the moisture as the evaluation index.

2. Experimental Results

① Freeze-Drying Prescription of rLZ-8 and Mutants Thereof

According to results shown in Table 12, at a high temperature condition, each stabilizer has little effect on the rLZ-8 that each index after 10 days is slightly decreased; and thus the stabilizers can all be applied in the subsequent prescription screening.

TABLE 12

Influences of stabilizers on rLZ-8

| Sample + stabilizer | 0 day | | | 5 days | | | 10 days | | |
|---|---|---|---|---|---|---|---|---|---|
| | Content (mg) | Purity (%) | Activity (IC50) | Content (mg) | Purity (%) | Activity (IC50) | Content (mg) | Purity (%) | Activity (IC50) |
| rLZ-8 + mannitol | 10.11 | 99.75% | 1.197 | 10.05 | 99.71% | 1.188 | 10.01 | 99.69% | 1.191 |
| rLZ-8 + lactose | 10.09 | 99.77% | 1.186 | 10.04 | 99.72% | 1.179 | 10.02 | 99.65% | 1.175 |

TABLE 12-continued

| | Influences of stabilizers on rLZ-8 | | | | | | | | |
|---|---|---|---|---|---|---|---|---|---|
| | 0 day | | | 5 days | | | 10 days | | |
| Sample + stabilizer | Content (mg) | Purity (%) | Activity (IC50) | Content (mg) | Purity (%) | Activity (IC50) | Content (mg) | Purity (%) | Activity (IC50) |
| rLZ-8 + mycose | 10.13 | 99.82% | 1.188 | 10.07 | 99.80% | 1.184 | 10.04 | 99.77% | 1.185 |

According to results shown in Table 13, at a high temperature condition, each surfactant has little effect on the rLZ-8 that each index after 10 days is slightly decreased; and thus the surfactants can all be applied in the subsequent prescription screening.

TABLE 13

| | Influences of surfactants on rLZ-8 | | | | | | | | |
|---|---|---|---|---|---|---|---|---|---|
| | 0 day | | | 5 days | | | 10 days | | |
| Sample + surfactant | Content (mg) | Purity (%) | Activity (IC50) | Content (mg) | Purity (%) | Activity (IC50) | Content (mg) | Purity (%) | Activity (IC50) |
| 1 | 10.07 | 99.65% | 1.177 | 10.04 | 99.62% | 1.168 | 10.02 | 99.61% | 1.166 |
| 2 | 10.08 | 99.57% | 1.184 | 10.04 | 99.55% | 1.179 | 10.03 | 99.53% | 1.172 |

Experimental results of prescription combination screening are showed in Table 14. The data indicate that: during screening process, indexes of the $3^{rd}$, $6^{th}$ and $9^{th}$ prescriptions have the relatively large change; compared with the $4^{th}$, $5^{th}$, $7^{th}$ and $8^{th}$ prescriptions, insoluble particle amounts and change amounts of the $1^{st}$ and $2^{nd}$ prescriptions have no obvious change; the $4^{th}$, $5^{th}$, $7^{th}$ and $8^{th}$ prescriptions contain surfactant, which may affect the subsequent toxicity test. The $1^{st}$ and $2^{nd}$ prescriptions can be used as the standby prescriptions, but the injectable lactose in the $2^{nd}$ prescription is difficult to obtain. Thus, the $1^{st}$ prescription is selected as the freeze-drying prescription.

TABLE 14

| | Screening results of freeze-drying prescriptions of rLZ-8 | | | | | | | | |
|---|---|---|---|---|---|---|---|---|---|
| | 0 day | | | 5 days | | | 10 days | | |
| Prescription number | Activity (IC50) | Insoluble particle (10 μm\25 μm) | Purity (%) | Activity (IC50) | Insoluble particle (10 μm\25 μm) | Purity (%) | Activity (IC50) | Insoluble particle (10 μm\25 μm) | Purity (%) |
| 1 | 1.177 | 47.2\19.3 | 99.65% | 1.186 | 48.4\19.6 | 99.47% | 1.179 | 47.9\21.6 | 99.45% |
| 2 | 1.184 | 50.2\19.6 | 99.57% | 1.187 | 51.3\18.7 | 99.43% | 1.192 | 52.2\20.6 | 99.42% |
| 3 | 1.167 | 49.3\18.3 | 99.32% | 1.341 | 120.5\40.2 | 95.42% | 1.573 | 300.6\0.5 | 92.31% |
| 4 | 1.188 | 48.5\19.3 | 99.41% | 1.184 | 47.5\19.4 | 99.36% | 1.124 | 44.3\18.9 | 99.54% |
| 5 | 1.171 | 57.4\22.4 | 99.28% | 1.177 | 52.1\23.2 | 99.18% | 1.167 | 58.5\24.5 | 99.21% |
| 6 | 1.164 | 52.1\23.6 | 99.34% | 1.376 | 53.3\25.6 | 95.42% | 1.752 | 52.8\28.8 | 92.31% |
| 7 | 1.182 | 51.3\24.8 | 99.53% | 1.187 | 55.5\28.8 | 99.63% | 1.178 | 53.4\29.6 | 99.55% |
| 8 | 1.183 | 52.4\28.9 | 99.76% | 1.184 | 56.8\21.6 | 99.46% | 1.189 | 54.2\26.5 | 99.66% |
| 9 | 1.194 | 55.2\27.5 | 99.45% | 1.401 | 58.4\28.8 | 95.42% | 1.886 | 56.3\29.3 | 92.31% |

② Freeze-Drying Process of rLZ-8 and Mutants Thereof

Figure 18:
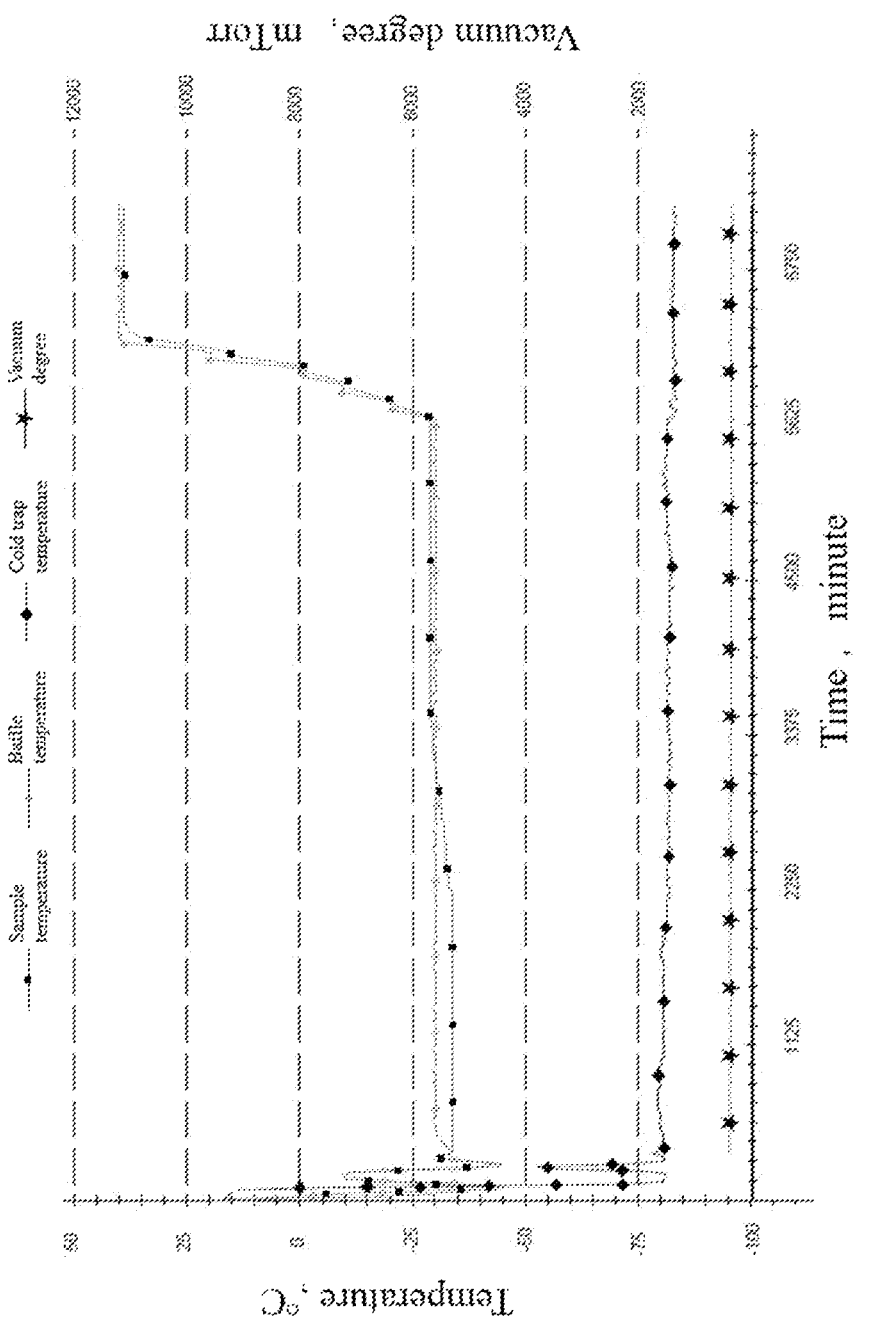
FIG. 18 shows freeze-drying process curves of the rLZ-8 according to a thirteenth preferred embodiment of the present invention.

Through exploring the freeze-drying condition, the optimal freeze-drying process is determined that: for the sublimation drying, the drying temperature is −30° C., the vacuum degree is 300 mTorr, and the drying time is 90 hours; for the vacuum drying, the drying temperature is 40° C., the vacuum degree is 250 mTorr, the drying time is 30 hours. FIG. 18 shows freeze-drying curves; and at the above condition, both of the character and the moisture of the freeze-drying sample reaches the standard.

With the same freeze-drying prescription and the same freeze-drying process, the rLZ-8 mutants can also obtain the freeze-dried powders with the character and the moisture reaching the standard.

SEQUENCE LISTING

```
<160> NUMBER OF SEQ ID NOS: 2

<210> SEQ ID NO 1
<211> LENGTH: 111
<212> TYPE: PRT
<213> ORGANISM: Artificial Sequence
<220> FEATURE:
<223> OTHER INFORMATION: The original sequence of the mutants is from
      the immunoregulatory protein of Ganoderma lucidum. The sequences
      of the mutants in this invention were synthesized in the
      laboratory.
<220> FEATURE:
<221> NAME/KEY: VARIANT
<222> LOCATION: (6)..(9)
<223> OTHER INFORMATION: The sequences were synthesized in the
      laboratory.
<220> FEATURE:
<221> NAME/KEY: VARIANT
<222> LOCATION: (16)..(20)
<223> OTHER INFORMATION: The sequences were synthesized in the
      laboratory.
<220> FEATURE:
<221> NAME/KEY: VARIANT
<222> LOCATION: (41)..(46)
<223> OTHER INFORMATION: The sequences were synthesized in the
      laboratory.
<220> FEATURE:
<221> NAME/KEY: VARIANT
<222> LOCATION: (68)..(74)
<223> OTHER INFORMATION: The sequences were synthesized in the
      laboratory.

<400> SEQUENCE: 1

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
                20                  25                  30

Phe Ile Asp Thr Val Thr Phe Pro Lys Val Leu Thr Asp Lys Ala Tyr
            35                  40                  45

Thr Tyr Arg Val Ala Val Ser Gly Arg Asn Leu Gly Val Lys Pro Ser
        50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
            100                 105                 110

<210> SEQ ID NO 2
<211> LENGTH: 14
<212> TYPE: PRT
<213> ORGANISM: Artificial Sequence
<220> FEATURE:
<223> OTHER INFORMATION: alpha helix amino acid sequence; residues 2-15
      of SEQ ID NO: 1
```

```
<400> SEQUENCE: 2

Ser Asp Thr Ala Leu Ile Phe Arg Leu Ala Trp Asp Val Lys
1               5                   10
```

What is claimed is:

1. A Lingzhi-8 (LZ-8; SEQ ID NO: 1) mutant, wherein the LZ-8 mutant comprises a mutation selected from the group consisting of:
   (1) the amino acid D at position 70 is replaced with K (D70K);
   (2) the amino acid K at position 46 is replaced with E (K46E);
   (3) the amino acid L at position 17 is replaced with K and the amino acid D at position 70 is replaced with K (L17K and D70K);
   (4) the amino acid D at position 20 is replaced with H (D20H);
   (5) the amino acid L at position 17 is replaced with K (L17K);
   (6) the amino acid K at position 46 is replaced with E and the amino acid K at position 74 is replaced with E (K46E and K74E); and
   (7) the amino acid D at position 20 is replaced with H and the amino acid D at position 70 is replaced with K (D20H and D70K).

2. The LZ-8 mutant of claim 1, wherein: the mutant is obtained through a recombinant expression system selected from the group consisting of: a prokaryotic expression system, a fungal expression system, and a mammalian cell expression system.

3. A composition comprising the LZ-8 mutant of claim 1, wherein said composition is a freeze-dried powder, injection solution, tablet, or inhalant.

4. A method for treating abnormal EGFR-expressed tumors in a subject, comprising administering a composition which comprises a therapeutically effective amount of the LZ-8 mutant of claim 1.

5. The method of claim 4, wherein the subject is being treated for a liver cancer.

6. The method of claim 4, wherein the subject is being treated for lung cancer.

7. The method of claim 4, wherein the subject is being treated for breast cancer.

8. The method of claim 4, wherein the subject is being treated for rectocolonic cancer.

9. The method of claim 4, wherein the composition is administered orally, subcutaneously, or intravenously.

* * * * *